US010563189B2

(12) United States Patent
Basler et al.

(10) Patent No.: US 10,563,189 B2
(45) Date of Patent: Feb. 18, 2020

(54) COMPOSITIONS AND METHODS COMPRISING VARIANT MICROBIAL PROTEASES

(71) Applicant: Danisco US Inc., Palo Alto, CA (US)

(72) Inventors: Joshua R. Basler, Palo Alto, CA (US); Luis G. Cascao-Pereira, Redwood City, CA (US); David A. Estell, San Francisco, CA (US); James T. Kellis, Jr., San Carlos, CA (US)

(73) Assignee: The Procter & Gamble Company, Cincinnati, OH (US)

( * ) Notice: Subject to any disclaimer, the term of this patent is extended or adjusted under 35 U.S.C. 154(b) by 203 days.

(21) Appl. No.: 14/537,761

(22) Filed: Nov. 10, 2014

(65) Prior Publication Data

US 2015/0064767 A1    Mar. 5, 2015

Related U.S. Application Data

(62) Division of application No. 12/996,564, filed as application No. PCT/US2009/046066 on Jun. 3, 2009, now abandoned.

(60) Provisional application No. 61/059,695, filed on Jun. 6, 2008.

(51) Int. Cl.
| | |
|---|---|
| *C12N 9/54* | (2006.01) |
| *C11D 3/386* | (2006.01) |
| *C12N 9/52* | (2006.01) |
| *A23K 20/189* | (2016.01) |
| *C11D 11/00* | (2006.01) |

(52) U.S. Cl.
CPC .............. *C12N 9/54* (2013.01); *A23K 20/189* (2016.05); *C11D 3/386* (2013.01); *C11D 3/38681* (2013.01); *C11D 11/0017* (2013.01); *C12N 9/52* (2013.01); *C12Y 304/21062* (2013.01)

(58) Field of Classification Search
CPC .......... C12N 9/54; C12N 9/52; A23K 20/189; C11D 11/0017; C11D 3/386; C11D 3/38681; C12Y 304/21062
See application file for complete search history.

(56) References Cited

U.S. PATENT DOCUMENTS

| | | | |
|---|---|---|---|
| 4,430,243 A | 2/1984 | Bragg | |
| 4,435,307 A | 3/1984 | Barbasgaard et al. | |
| 4,683,195 A | 7/1987 | Mullis et al. | |
| 4,683,202 A | 7/1987 | Mullis et al. | |
| 4,965,188 A | 10/1990 | Mullis et al. | |
| 4,977,252 A | 12/1990 | Chiu | |
| RE34,606 E | 5/1994 | Estell et al. | |
| 5,340,735 A | 8/1994 | Christianson et al. | |
| 5,354,559 A | 10/1994 | Morehouse | |
| 5,427,936 A | 6/1995 | Moeller et al. | |
| 5,486,303 A | 1/1996 | Capeci et al. | |
| 5,489,392 A | 2/1996 | Capeci et al. | |
| 5,500,364 A | 3/1996 | Christenson et al. | |
| 5,516,448 A | 5/1996 | Capeci et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,646,101 A | 7/1997 | MacBeath | |
| 5,677,163 A | 10/1997 | Mainzer et al. | |
| 5,677,272 A | 10/1997 | Ghosh et al. | |
| 5,679,630 A | 10/1997 | Baeck et al. | |
| 5,686,014 A | 11/1997 | Baillely et al. | |
| 5,691,297 A | 11/1997 | Nassano et al. | |
| 5,695,679 A | 12/1997 | Christie et al. | |
| 5,698,504 A | 12/1997 | Christie et al. | |
| 5,700,676 A | 12/1997 | Bott et al. | |
| 5,705,464 A | 1/1998 | Scheper et al. | |
| 5,710,115 A | 1/1998 | Patel et al. | |
| 5,801,039 A | 9/1998 | Maurer et al. | |
| 5,855,625 A | 1/1999 | Maurer et al. | |
| 5,874,276 A | 2/1999 | Fowler et al. | |
| 5,879,564 A | 3/1999 | Bianchetti et al. | |
| 5,935,826 A | 8/1999 | Blue et al. | |
| 5,955,340 A | 9/1999 | Bott et al. | |
| 6,017,871 A | 1/2000 | Baeck et al. | |
| 6,225,464 B1 | 5/2001 | Hiler, II et al. | |
| 6,306,812 B1 | 10/2001 | Perkins et al. | |
| 6,312,936 B1 | 11/2001 | Poulose et al. | |
| 6,326,348 B1 | 12/2001 | Vinson et al. | |

(Continued)

FOREIGN PATENT DOCUMENTS

| | | |
|---|---|---|
| EP | 0258068 | 3/1986 |
| EP | 0214761 | 3/1987 |

(Continued)

OTHER PUBLICATIONS

Extended European Search Report for European Patent Application 13171129.3 dated Nov. 21, 2013.

(Continued)

*Primary Examiner* — Paul J Holland

(74) *Attorney, Agent, or Firm* — Andres E. Velarde; Melissa G. Krasovec

(57) ABSTRACT

The present invention provides variant subtilisins and compositions comprising at least one variant subtilisin set forth herein, as well as methods for using these variants and compositions. In some embodiments, the present invention provides variant subtilisins suitable for laundry cleaning applications.

8 Claims, No Drawings

Specification includes a Sequence Listing.

(56) References Cited

U.S. PATENT DOCUMENTS

| | | | |
|---|---|---|---|
| 6,376,450 B1 | 4/2002 | Ghosh et al. | |
| 6,436,690 B1* | 8/2002 | Brode, III | A61K 8/66 435/222 |
| 6,440,991 B1 | 8/2002 | Zhu et al. | |
| 6,461,849 B1 | 10/2002 | Olsen et al. | |
| 6,482,628 B1 | 11/2002 | Poulose et al. | |
| 6,509,021 B1 | 1/2003 | Weiss et al. | |
| 6,566,114 B1 | 5/2003 | Kauppinen et al. | |
| 6,582,914 B1 | 6/2003 | Caldwell et al. | |
| 6,586,221 B2 | 7/2003 | Graycar et al. | |
| 6,602,842 B2 | 8/2003 | Cuperus et al. | |
| 6,605,458 B1 | 8/2003 | Hansen et al. | |
| 6,610,642 B2 | 8/2003 | Ghosh et al. | |
| 6,773,907 B2* | 8/2004 | Hansen | C11D 3/38681 435/220 |
| 6,897,049 B1 | 5/2005 | Estell et al. | |
| 6,929,939 B2 | 8/2005 | Estell et al. | |
| 7,910,115 B2 | 3/2011 | Nakatsugawa et al. | |
| 8,535,927 B1 | 9/2013 | Jones et al. | |
| 8,728,790 B2* | 5/2014 | Basler | C12N 9/52 435/226 |
| 8,785,171 B2* | 7/2014 | Souter | C11D 3/38609 435/212 |
| 9,157,052 B2* | 10/2015 | Basler | C12N 9/52 |
| 2003/0077807 A1* | 4/2003 | Graycar | C12N 9/54 435/222 |
| 2003/0191039 A1 | 10/2003 | Aasylng et al. | |
| 2004/0147008 A1* | 7/2004 | Draborg | C12N 9/54 435/226 |
| 2005/0054843 A1* | 3/2005 | Estell | A61K 8/66 536/23.2 |
| 2005/0148059 A1* | 7/2005 | Estell | A61K 8/66 435/221 |
| 2005/0181446 A1 | 8/2005 | Roggen et al. | |
| 2005/0202552 A1 | 9/2005 | Estell et al. | |
| 2005/0239043 A1 | 10/2005 | Harding | |
| 2006/0014265 A1 | 1/2006 | Ferrari et al. | |
| 2008/0009431 A1* | 1/2008 | Boutique | C11D 3/33 510/393 |
| 2008/0145353 A1 | 6/2008 | Amin et al. | |
| 2008/0293610 A1 | 11/2008 | Shaw et al. | |
| 2010/0192985 A1 | 8/2010 | Aehle et al. | |
| 2011/0251073 A1* | 10/2011 | Cascao-Pereira | C11D 3/38681 506/2 |
| 2011/0256609 A1* | 10/2011 | Basler | C11D 3/38681 435/221 |
| 2011/0256610 A1* | 10/2011 | Alekseyev | C11D 3/38681 435/222 |
| 2014/0193888 A1* | 7/2014 | Souter | C11D 3/38609 435/263 |
| 2015/0056682 A1* | 2/2015 | Alekseyev | C11D 3/38681 435/221 |
| 2015/0159147 A1* | 6/2015 | Basler | C11D 3/38681 435/222 |
| 2015/0247140 A1* | 9/2015 | Alekseyev | C11D 3/38681 435/222 |
| 2016/0083710 A1* | 3/2016 | Basler | C12N 9/52 435/221 |

FOREIGN PATENT DOCUMENTS

| | | |
|---|---|---|
| EP | 0218272 | 4/1987 |
| EP | 0238023 | 9/1987 |
| EP | 0305216 | 3/1989 |
| EP | 0331376 | 9/1989 |
| EP | 0495257 | 7/1992 |
| GB | 1296839 | 11/1972 |
| GB | 1372034 | 10/1974 |
| JP | 64/074992 | 3/1989 |
| WO | WO88/09367 | 12/1988 |
| WO | WO89/06270 | 7/1989 |
| WO | WO90/09446 | 8/1990 |
| WO | WO91/00334 | 1/1991 |
| WO | WO92/21760 | 12/1992 |
| WO | WO94/12621 | 6/1994 |
| WO | WO95/01426 | 1/1995 |
| WO | WO95/07991 | 3/1995 |
| WO | WO95/23221 | 8/1995 |
| WO | WO97/11151 | 2/1997 |
| WO | WO99/34011 | 7/1999 |
| WO | WO00/32601 | 6/2000 |
| WO | WO02/14490 | 2/2002 |
| WO | WO02/077187 | 10/2002 |
| WO | WO03/062381 | 7/2003 |
| WO | WO05/052146 | 6/2005 |
| WO | WO05/056782 | 6/2005 |

OTHER PUBLICATIONS

U.S. Appl. No. 11/583,334, filed Oct. 19, 2006, Wolfgang et al.

Altschul, S.F., et al., "Basic Local Alignment Search Tool." *J. Mol. Biol.* 215: 403-410, 1990.

Altschul, S.F., et al., "Basic Local Alignment Statistics." *Meth. Enzymol.* 266:460-480, 1996.

Bloom, J.D., et al., "Evolving strategies for enzyme engineering." *Curr. Opin. Struct. Biol.* 15: 447-452, 2005.

Bloom, J.D., et al., "Protein stability promotes evolvability." *Proc. Natl. Acad. Sci. USA* 103: 5869-5874, 2006.

Bolivar, F., et al., "Construction and Characterization of New Cloning Vehicles: I. Ampicillin-resistant Derivatives of the Plasmid pMB9." *Gene* 2: 95-113, 1977.

Bryan, P.N., "Protein engineering of subtilisin." *Biochimica et Biophysica Acta* 1543: 203-222, 2000.

Dartois, V., et al., "Cloning, nucleotide sequence and expression in *Escherichia coli* of a lipase gene from *Bacillus subtilis* 168." *Biochem. Biophys. Acta* 1131: 253-260, 1992.

Database Geneseq [Online], "Wild type subtilisin." Database Accession No. AAY43221, XP 002544118 (Jan. 13, 2000).

Database UniProt [Online] "Intracellular serine protease." XP002545418; Tebo, B., et al., Database Accession No. A6CNY8 (Jul. 24, 2007).

Database UniProt [Online] "SptC." XP002545419; Shi, W, et al., Database Accession No. A1X2U6 (Feb. 6, 2007).

Del Mar, E.G., et al., "A Sensitive New Substrate for Chymotrypsin." *Anal. Biochem.* 99: 316-320, 1979.

Devereux, J., et al., "A comprehensive set of sequence analysis programs for the VAX." *Nucl. Acid Res.* 12: 387-395, 1984.

Dynan, W.S., et al., "Control of eukaryotic messenger RNA synthesis by sequence-specific DNA-binding proteins." *Nature* 316: 774-778, 1985.

Estell, D., et al., "Site-directed mutagenesis of the active site of Subtilisin BPN'." In *The World Biotech Report 1984*, vol. 2: USA, The Proceedings of Biotech 84, USA, Online Publications, Middlesex, England; NY, NY; 1984, pp. 181-187.

Feng, D.-F., "Progressive Sequence Alignment as a Prerequisite to Correct Phylogenetic Trees." *J. Mol. Evol.* 25: 351-360, 1987.

Ferrari, E., et al., "Genetics," In Bacillus, Hardwood (ed.), Plenum Publishing Corp., pp. 57-72, 1989.

Ferrari, E. et al., "Construction and Properties of an Integrable Plasmid for *Bacillus subtilis*." *J. Bacteriol.* 154: 1513-1515, 1983.

Guo, H.H., et al., "Protein tolerance to random amino acid change." *Proc. Natl. Acad. Sci. USA* 101: 9205-9210, 2004.

Haas, M.J., et al., "Cloning, expression and characterization of a cDNA encoding a lipase from *Rhizopus delemar*." *Gene* 109: 117-113, 1991.

Heinz, D.W., et al., "Changing the Inhibitory Specificity and Function of the Proteinase Inhibitor Eglin c by Site-Directed Mutagenesis: Functional and Structural Investigation." *Biochemistry* 31: 8755-8766, 1992.

Higgins, D.G., et al., "Fast and sensitive multiple sequence alignments on a microcomputer." *CABIOS* 5: 151-153, 1989.

Horinouchi, S., et al. "Nucleotide Sequence and Functional Map of pC194, a Plasmid That Specifies Inducible Chloramphenicol Resistance." *J. Bacteriol.* 150: 815-825, 1982.

(56) References Cited

OTHER PUBLICATIONS

Kalisz, "Microbial Proteinases." In *Advances in Biochemical Engineering/Biotechnology*, vol. 36, Flechter, A. (ed.), pp. 2-65, 1988.

Karlin, S., et al., "Applications and statistics for multiple high-scoring segment s in molecular sequences." *Proc. Natl. Acad. Sci. USA* 90: 5873-5877, 1993.

Kato, R., et al., "Novel Strategy for Protein Exploration: High-throughput Screening Assisted with Fuzzy Neural Network." *J. Mol. Biol.* 351: 683-692, 2005.

Kugimiya, W., et al., "Cloning and Sequence Analysis of cDNA encoding *Rhizopus niveus* Lipase." *Biosci. Biotech. Biochem.* 56(5): 716-719, 1992.

McKenzie, T., et al., "The Nucleotide Sequence of pUB110: Some Salient Features in Relation to Replication and Its Regulation," *Plasmid* 15: 93-103, 1986.

Needleman, S.B., et al., "A General Method Applicable to the Search for Similarities in the Amino Add Sequence of Two Proteins." *J. Mol. Biol.* 48: 443-453, 1970.

Neidhardt, F.C., et al., "Culture Medium for Enterobacteria." *J. Bacteriol.*, 119: 736-747, 1974.

Pearson, W.R., et al., "Improved tools for biological sequence comparison," *Proc. Natl. Acad. Sci. USA* 85: 2444-2448, 1988.

Pierce, N.A., et al., "Protein Design is NP-hard." *Protein Engineer* 15: 779-782, 2002.

Reetz, M.T., et al., "Expanding the Range of Substrate Acceptance of Enzymes: Combinatorial Active-Site Saturation Test." *Agnew. Chem. Int. Ed.* 44:4192-4196, 2005.

Rollence, M., et al., "Engineering Thermostabillity in Subtilisin in Vitro Mutagenesis." *CRC Critical Review in Biotechnology*, CRC Press, Boca Raton, FL, 8(3): 217-224, 1988.

Sandberg, W.S., et al., "Engineering multiple properties of a protein by combinatorial mutagenesis." *Proc. Natl. Acad. Sci. USA* 90: 8367-8371, 1993.

Schimada, Y., et al., "cDNA Molecular Cloning of *Geotrichum candidum* Lipase." *J. Biochem.* 106: 383-388, 1989.

Smith, T.F., et al., "Comparison of Biosequences." *Adv. Appl. Math.* 2: 482-489, 1981.

Wells, J.A., et al., "Cassette mutagenesis: an efficient method for generation of multiple mutations at defined sites," *Gene* 34: 315-323, 1985.

Yamaguchi, S., et al., "Cloning and structure of the mono- and diacylglyceral lipase-encoding gene from *Penicillium camembertil* U-150." *Gene* 103: 61-67, 1991.

International Preliminary Report on Patentability for International Application No. PCT/US09/46066 dated Dec. 6, 2010.

International Search Report and the Written Opinion of the International Searching Authority for International Application No. PCT/US09/46066 dated Mar. 5, 2010.

Partial European Search Report for European Patent Application No. EP13171129.3 dated Aug. 27, 2013.

\* cited by examiner

SEQUENCE LISTING

```
<160> NUMBER OF SEQ ID NOS: 2

<210> SEQ ID NO 1
<211> LENGTH: 275
<212> TYPE: PRT
<213> ORGANISM: Bacillus amyloliquefaciens

<400> SEQUENCE: 1

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
        130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175
```

```
Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
                260                 265                 270

Ala Ala Gln
        275

<210> SEQ ID NO 2
<211> LENGTH: 4
<212> TYPE: PRT
<213> ORGANISM: Artificial
<220> FEATURE:
<223> OTHER INFORMATION: synthetic reagent

<400> SEQUENCE: 2

Ala Ala Pro Phe
1
```

COMPOSITIONS AND METHODS COMPRISING VARIANT MICROBIAL PROTEASES

CROSS REFERENCE TO RELATED APPLICATION

This application is a divisional application of U.S. patent application Ser. No. 12/996,564, filed Jun. 14, 2011, which is a U.S. National Stage Application of International Application No. PCT/US2009/046066, filed Jun. 3, 2009, which claims the benefit of U.S. Provisional Application No. 61/059,695, filed Jun. 6, 2008, which are herein incorporated by reference in their entireties.

FIELD OF THE INVENTION

The present invention provides variant subtilisins and compositions comprising at least one variant subtilisin set forth herein, as well as methods for using these variants and compositions. In particular, the present invention provides variant proteases suitable for laundry cleaning applications.

BACKGROUND OF THE INVENTION

Serine proteases are a subgroup of carbonyl hydrolases comprising a diverse class of enzymes having a wide range of specificities and biological functions. Much research has been conducted on the subtilisins, due largely to their usefulness in cleaning and feed applications. Additional work has been focused on the adverse environmental conditions (e.g., exposure to oxidative agents, chelating agents, extremes of temperature and/or pH) which can adversely impact the functionality of these enzymes in various applications. Nonetheless, there remains a need in the art for enzyme systems that are able to resist these adverse conditions and retain or have improved activity over those currently known in the art.

SUMMARY OF THE INVENTION

The present invention provides variant subtilisins and compositions comprising at least one variant subtilisin set forth herein, as well as methods for using these variants and compositions. In some embodiments, the present invention provides variant proteases suitable for laundry cleaning applications.

The present invention provides isolated subtilisin variants comprising at least one set of the following substitution sets: G97A-G128A-Y217Q, G97A-L126A-G128A, G97A-L126A-G128A-Y217Q, G97A-L126A-Y217Q, G97A-M124V-G128A, G97A-M124V-G128A-Y217Q, G97A-M124V-L126A, G97A-M124V-L126A-G128A, G97A-M124V-L126A-Y217Q, G97A-M124V-Y217Q, G97A-N123G-G128A, G97A-N123G-G128A-Y217Q, G97A-N123G-L126A, G97A-N123G-L126A-G128A, G97A-N123G-L126A-Y217Q, G97A-N123G-M124V, G97A-N123G-M124V-G128A, G97A-N123G-M124V-L126A, G97A-N123G-M124V-Y217Q, G97A-N123G-Y217Q, L126A-G128A-Y217Q, L96T-G128A-Y217Q, L96T-G97A-G128A, L96T-G97A-G128A-Y217Q, L96T-G97A-L126A, L96T-G97A-L126A-G128A, L96T-G97A-L126A-Y217Q, L96T-G97A-M124V, L96T-G97A-M124V-G128A, L96T-G97A-M124V-L126A, L96T-G97A-M124V-Y217Q, L96T-G97A-N123G, L96T-G97A-N123G-G128A, L96T-G97A-N123G-L126A, L96T-G97A-N123G-M124V, L96T-G97A-N123G-Y217Q, L96T-G97A-Y217Q, L96T-L126A-G128A, L96T-L126A-G128A-Y217Q, L96T-L126A-Y217Q, L96T-M124V-G128A, L96T-M124V-G128A-Y217Q, L96T-M124V-L126A, L96T-M124V-L126A-G128A, L96T-M124V-L126A-Y217Q, L96T-M124V-Y217Q, L96T-N123G-G128A, L96T-N123G-G128A-Y217Q, L96T-N123G-L126A, L96T-N123G-L126A-G128A, L96T-N123G-L126A-Y217Q, L96T-N123G-M124V, L96T-N123G-M124V-G128A, L96T-N123G-M124V-L126A, L96T-N123G-M124V-Y217Q, L96T-N123G-Y217Q, M124V-G128A-Y217Q, M124V-L126A-G128A, M124V-L126A-G128A-Y217Q, M124V-L126A-Y217Q, N123G-G128A-Y217Q, N123G-L126A-G128A, N123G-L126A-G128A-Y217Q, N123G-L126A-Y217Q, N123G-M124V-G128A, N123G-M124V-G128A-Y217Q, N123G-M124V-L126A, N123G-M124V-L126A-G128A, N123G-M124V-L126A-Y217Q, N123G-M124V-Y217Q, N62Q-G128A-Y217Q, N62Q-G97A-G128A, N62Q-G97A-G128A-Y217Q, N62Q-G97A-L126A, N62Q-G97A-L126A-G128A, N62Q-G97A-L126A-Y217Q, N62Q-G97A-M124V, N62Q-G97A-M124V-G128A, N62Q-G97A-M124V-L126A, N62Q-G97A-M124V-Y217Q, N62Q-G97A-N123G, N62Q-G97A-N123G-G128A, N62Q-G97A-N123G-L126A, N62Q-G97A-N123G-M124V, N62Q-G97A-N123G-Y217Q, N62Q-G97A-Y217Q, N62Q-L126A-G128A, N62Q-L126A-G128A-Y217Q, N62Q-L126A-Y217Q, N62Q-L96T-G128A, N62Q-L96T-G128A-Y217Q, N62Q-L96T-G97A, N62Q-L96T-G97A-G128A, N62Q-L96T-G97A-L126A, N62Q-L96T-G97A-M124V, N62Q-L96T-G97A-N123G, N62Q-L96T-G97A-Y217Q, N62Q-L96T-L126A, N62Q-L96T-L126A-G128A, N62Q-L96T-L126A-Y217Q, N62Q-L96T-M124V, N62Q-L96T-M124V-G128A, N62Q-L96T-M124V-L126A, N62Q-L96T-M124V-Y217Q, N62Q-L96T-N123G, N62Q-L96T-N123G-G128A, N62Q-L96T-N123G-L126A, N62Q-L96T-N123G-M124V, N62Q-L96T-N123G-Y217Q, N62Q-L96T-Y217Q, N62Q-M124V-G128A, N62Q-M124V-G128A-Y217Q, N62Q-M124V-L126A, N62Q-M124V-L126A-G128A, N62Q-M124V-L126A-Y217Q, N62Q-M124V-Y217Q, N62Q-N123G-G128A, N62Q-N123G-G128A-Y217Q, N62Q-N123G-L126A, N62Q-N123G-L126A-G128A, N62Q-N123G-L126A-Y217Q, N62Q-N123G-M124V, N62Q-N123G-M124V-G128A, N62Q-N123G-M124V-L126A, N62Q-N123G-M124V-Y217Q, and N62Q-N123G-Y217Q, wherein the substitutions are at positions equivalent to the positions of BPN' subtilisin set forth in SEQ ID NO:1.

The present invention also provides isolated subtilisin variants comprising at least one set of the following substitution sets: G97N-G128A-Y217M, G97G-G128S-Y217E, G97A-G128A-Y217Q, G97M-G128S-Y217E, G97A-G128S-Y217Q, G97D-G128S-Y217Q, G97M-G128G-Y217M, G97G-G128S-Y217Q, G97S-G128S-Y217Q, G97G-G128A-Y217Q, G97S-G128A-Y217E, G97A-G128S-Y217L, G97A-G128A-Y217N, G97Q-G128S-Y217L, G97A-G128A-Y217M, G97A-G128A-Y217S, G97D-G128A-Y217Q, G97M-G128S-Y217Q, G97Q-G128G-Y217D-S87Y, G97S-G128A-Y217N, G97A-G128S-Y217T, G97D-G128S-Y217E, G97D-G128A-Y217L, G97G-G128S-Y217E-S78P-A272T, G97T-G128S-Y217D, G97D-G128A-Y217I, G97Q-G128S-Y217Q, G97G-G128A-Y217D, G97Q-G128A-Y217N, G97S-G128A-Y217M, G97S-G128S-Y217N, G97S-G128S-Y217M, G97E-G128S-Y217M, G97S-G128P-Y217Q, G97T-G128S-Y217Q, G97D-G128S-Y217Q-A73T, G97E-G128S-Y217N, G97G-G128A-Y217I, G97Q-G128A-Y217D, G97Q-G128S-Y217M, G97R-G128T-Y217Q-S162P, G97S-G128S-Y217D, G97T-G128P-Y217I, G97Q-G128G-Y217E, G97C-G128G-Y217N, G97D-G128S-

Y217H, G97M-G128S-Y217L, G97M-G128S-Y217N, G97S-G128S-Y217E, G97M-G128S-Y217I, G97A-G128P-Y217A, G97R-G128S-Y217D, G97D-G128A-Y217D, G97V-G128G-Y217D, G97V-G128G-Y217E, G97A-G128G-Y217T, G97G-G128N-Y217L, G97D-G128A-Y217T, G97M-G128A-Y217E, and G97M-G128A-Y217N, wherein the substitutions are at positions equivalent to the positions of BPN' subtilisin set forth in SEQ ID NO:1.

The present invention further provides isolated subtilisin variants comprising at least one set of the following substitution sets: S24R-S87D-Q206E, P40E-A144K-K213L, N61E-P129E-S159K, S87D-S162K-K265N, S87D-T242R-Q275E, N61E-Q103E-N240K, S87D-T242R-K265N, N62R-K265N-Q275E, P129E-S145D-N240K, P129E-P239R-K265N, Q103E-P129E-T242R, P40E-N61E-S87D-S162K-T242R, S24R-N62R-S87D-S145D-K265N, P40E-N62R-S87D-Q103E-S162K, S24R-P40E-S145D-S159K-K213L, S24R-S87D-A144K-K265N-Q275E, N61E-P129E-S162K-K213L-N240K, N61E-S145D-S162K-K213L-T242R, S87D-A144K-S145D-S159K-Q275E, S24R-P129E-Q206E-N240K-K265N, N61E-Q103E-A144K-K213L-T242R, N62R-S159K-Q206E-K265N-Q275E, S24R-Q103E-P129E-N240K-K265N, N61E-Q103E-P129E-P239R-N240K, P129E-S145D-N240K-T242R-K265N, Q103E-S162K-Q206E-K213L-P239R, P40E-N61E-N62R-S87D-S159K-S162K-K265N, S24R-P40E-N61E-A144K-Q206E-K213L-T242R, P40E-N61E-S87D-P129E-S159K-S162K-T242R, P40E-N62R-S87D-S145D-S159K-S162K-Q275E, P40E-N62R-S87D-Q103E-A144K-S159K-Q275E, P40E-N62R-S87D-S159K-S162K-K265N-Q275E, P40E-N61E-P129E-A144K-S162K-K213L-N240K, P40E-N61E-Q103E-A144K-S159K-S162K-Q275E, P40E-N61E-Q103E-S159K-S162K-K213L-P239R, P40E-N61E-Q103E-S159K-S162K-K213L-N240K, N62R-S87D-P129E-S145D-S159K-S162K-Q275E, S24R-N61E-Q103E-P129E-K213L-N240K-T242R, P40E-N62R-S145D-S159K-S162K-Q206E-Q275E, N62R-S87D-S145D-S159K-S162K-K265N-Q275E, N61E-S87D-Q103E-S159K-S162K-K213L-T242R, S24R-N61E-Q103E-P129E-Q206E-P239R-N240K, S24R-N62R-P129E-S145D-P239R-K265N-Q275E, S24R-N62R-P129E-Q206E-N240K-K265N-Q275E, P40E-S145D-S159K-S162K-K213L-P239R-Q275E, N61E-Q103E-A144K-Q206E-K213L-N240K-T242R, S24R-Q103E-P129E-S145D-P239R-N240K-K265N, N61E-Q103E-P129E-K213L-P239R-N240K-T242R, N61E-Q103E-Q206E-K213L-P239R-N240K-T242R, S24R-P40E-N61E-S87D-Q103E-S159K-S162K-K213L-N240K, N61E-N62R-S87D-Q103E-S159K-S162K-K213L-T242R-Q275E, P40E-N62R-S87D-S145D-S159K-S162K-N240K-K265N-Q275E, N62R-S87D-S145D-S159K-S162K-K213L-N240K-K265N-Q275E, S24R-N61E-Q103E-P129E-Q206E-K213L-P239R-N240K-T242R, S24R-N61E-Q103E-P129E-S145D-P239R-N240K-T242R-K265N, N61E-S87D-Q103E-P129E-S159K-S162K-K213L-N240K-T242R, P40E-N61E-Q103E-P129E-A144K-K213L-P239R-N240K-T242R, S24R-Q103E-P129E-S145D-Q206E-P239R-N240K-T242R-K265N, N61E-Q103E-P129E-A144K-Q206E-K213L-P239R-N240K-T242R, S24R-P40E-N61E-S87D-Q103E-P129E-A144K-K213L-P239R-N240K-T242R, S24R-P40E-N61E-Q103E-P129E-A144K-K213L-P239R-N240K-T242R-K265N, S24R-P40E-N61E-Q103E-P129E-A144K-Q206E-K213L-P239R-N240K-T242R, S24R-P40E-N61E-Q103E-P129E-A144K-S145D-K213L-P239R-N240K-T242R, S24R-N61E-S87D-Q103E-P129E-A144K-Q206E-K213L-P239R-N240K-T242R, P40E-N61E-S87D-Q103E-S145D-S159K-S162K-K213L-P239R-N240K-T242R, S24R-P40E-N61E-Q103E-P129E-S162K-Q206E-K213L-P239R-N240K-T242R, S24R-N61E-Q103E-P129E-A144K-S145D-Q206E-K213L-P239R-N240K-T242R, P40E-N61E-Q103E-P129E-A144K-S162K-Q206E-K213L-P239R-N240K-T242R, S24R-N61E-Q103E-P129E-A144K-Q206E-K213L-P239R-N240K-T242R-K265N, and S24R-P40E-N61E-S87D-Q103E-P129E-A144K-S162K-Q206E-K213L-P239R-N240K-T242R, wherein wherein said substitutions are at positions equivalent to the positions of BPN' subtilisin set forth in SEQ ID NO:1.

The present invention also provides subtilisin variants comprising the substitutions G97A/G128A/Y217Q and further comprising at least one of the above substitution sets, and wherein the positions correspond to the positions of BPN' subtilisin of SEQ ID NO:1.

The present invention further provides isolated subtilisin variants comprising at least one set of the following substitution sets: S53G-F58G, S53G-S78N, S53G-Y104N, S53G-I111V, S53G-A114G, S53G-N117S, S53G-S125A, S53G-S132N, S53G-P239V, F58G-S78N, F58G-Y104N, F58G-I111V, F58G-A114G, F58G-N117S, F58G-S125A, F58G-S132N, F58G-P239V, S78N-Y104N, S78N-I111V, S78N-A114G, S78N-N117S, S78N-S125A, S78N-S132N, S78N-P239V, Y104N-I111V, Y104N-A114G, Y104N-N117S, Y104N-S125A, Y104N-S132N, Y104N-P239V, I111V-A114G, I111V-N117S, I111V-S125A, I111V-S132N, I111V-P239V, A114G-N117S, A114G-S125A, A114G-S132N, A114G-P239V, N117S-S125A, N117S-S132N, N117S-P239V, S125A-S132N, S125A-P239V, S132N-P239V, S53G-F58G-S78N, S53G-F58G-Y104N, S53G-F58G-I111V, S53G-F58G-A114G, S53G-F58G-N117S, S53G-F58G-S125A, S53G-F58G-S132N, S53G-F58G-P239V, S53G-S78N-Y104N, S53G-S78N-I111V, S53G-S78N-A114G, S53G-S78N-N117S, S53G-S78N-S125A, S53G-S78N-S132N, S53G-S78N-P239V, S53G-Y104N-I111V, S53G-Y104N-A114G, S53G-Y104N-N117S, S53G-Y104N-S125A, S53G-Y104N-S132N, S53G-Y104N-P239V, S53G-I111V-A114G, S53G-I111V-N117S, S53G-I111V-S125A, S53G-I111V-S132N, S53G-I111V-P239V, S53G-A114G-N117S, S53G-A114G-S125A, S53G-A114G-S132N, S53G-A114G-P239V, S53G-N117S-S125A, S53G-N117S-S132N, S53G-N117S-P239V, S53G-S125A-S132N, S53G-S125A-P239V, S53G-S132N-P239V, F58G-S78N-Y104N, F58G-S78N-I111V, F58G-S78N-A114G, F58G-S78N-N117S, F58G-S78N-S125A, F58G-S78N-S132N, F58G-S78N-P239V, F58G-Y104N-I111V, F58G-Y104N-A114G, F58G-Y104N-N117S, F58G-Y104N-S125A, F58G-Y104N-S132N, F58G-Y104N-P239V, F58G-I111V-A114G, F58G-I111V-N117S, F58G-I111V-S125A, F58G-I111V-S132N, F58G-I111V-P239V, F58G-A114G-N117S, F58G-A114G-S125A, F58G-A114G-S132N, F58G-A114G-P239V, F58G-N117S-S125A, F58G-N117S-S132N, F58G-N117S-P239V, F58G-S125A-S132N, F58G-S125A-P239V, F58G-S132N-P239V, S78N-Y104N-I111V, S78N-Y104N-A114G, S78N-Y104N-N117S, S78N-Y104N-S125A, S78N-Y104N-S132N, S78N-Y104N-P239V, S78N-I111V-A114G, S78N-I111V-N117S, S78N-I111V-S125A, S78N-I111V-S132N, S78N-I111V-P239V, S78N-A114G-N117S, S78N-A114G-S125A, S78N-A114G-S132N, S78N-A114G-P239V, S78N-N117S-S125A, S78N-N117S-S132N, S78N-N117S-P239V, S78N-S125A-S132N, S78N-S125A-P239V, S78N-S132N-P239V, Y104N-I111V-A114G, Y104N-I111V-N117S, Y104N-I111V-S125A, Y104N-I111V-S132N, Y104N-I111V-P239V, Y104N-A114G-N117S, Y104N-A114G-S125A, Y104N-A114G-S132N, Y104N-A114G-P239V, Y104N-N117S-S125A, Y104N-

N117S-S132N, Y104N-N117S-P239V, Y104N-S125A-S132N, Y104N-S125A-P239V, Y104N-S132N-P239V, I111V-A114G-N117S, I111V-A114G-S125A, I111V-A114G-S132N, I111V-A114G-P239V, I111V-N117S-S125A, I111V-N117S-S132N, I111V-N117S-P239V, I111V-S125A-S132N, I111V-S125A-P239V, I111V-S132N-P239V, A114G-N117S-S125A, A114G-N117S-S132N, A114G-N117S-P239V, A114G-S125A-S132N, A114G-S125A-P239V, A114G-S132N-P239V, N117S-S125A-S132N, N117S-S125A-P239V, N117S-S132N-P239V, S125A-S132N-P239V, N76D-D120H-K213N-M222Q, wherein wherein said substitutions are at positions equivalent to the positions of BPN' subtilisin set forth in SEQ ID NO:1.

The present invention also provides subtilisin variants comprising the substitutions G97A/G128A/Y217Q and further comprising at least one of the above substitution sets, and wherein the positions correspond to the positions of BPN' subtilisin of SEQ ID NO:1.

The present invention also provides isolated nucleic acids encoding the subtilisin variants set forth herein, as well as expression vectors comprising these nucleic acids, and host cells comprising these expression vectors.

The present invention further provides cleaning compositions comprising at least one of the subtilisin variant provided herein. In some embodiments, the cleaning compositions are laundry detergents. In some additional embodiments, the laundry detergent is a heavy duty liquid laundry detergent. In some further embodiments, the cleaning composition is a dish detergent. In some still further embodiments, the cleaning composition is a hard surface cleaning composition. In some additional embodiments, the cleaning compositions further comprise one or more additional enzymes or enzyme derivatives selected from the group consisting of hemicellulases, peroxidases, proteases, cellulases, xylanases, lipases, phospholipases, esterases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning compositions further comprise at least one stabilizing agent. In some further embodiments, the cleaning compositions comprise at least 0.0001 weight percent of at least one subtilisin variant provided herein and optionally, a suitable adjunct ingredient.

The present invention also provides methods for cleaning, comprising the steps of: contacting a surface and/or an article comprising a fabric with the cleaning compositions provided herein; and optionally washing and/or rinsing the surface or article.

The present invention further provides animal feeds comprising at least one subtilisin variant provided herein. The present invention also provides food processing compositions comprising at least one subtilisin variant provided herein.

DESCRIPTION OF THE INVENTION

The present invention provides variant subtilisins and compositions comprising at least one variant subtilisin set forth herein, as well as methods for using these variants and compositions. In particular, the present invention provides variant proteases suitable for laundry cleaning applications.

In some embodiments, the present invention provides means to produce variant subtilisins with various commercial applications where degradation or synthesis of polypeptides are desired, including cleaning compositions, as well as feed components, textile processing, leather finishing, grain processing, meat processing, food processing, preparation of protein hydrolysates, digestive aids, microbicidal compositions, bacteriostatic compositions, fungistatic compositions, and personal care products (e.g., oral care, hair care, and/or skin care).

The present invention further provides enzyme compositions have comparable or improved wash performance, as compared to presently used subtilisin proteases. In some embodiments, the present invention provides cleaning compositions comprising at least one subtilisin variant provided herein. In some embodiments, the cleaning composition is a laundry detergent. In some embodiments, the laundry detergent is a cold water detergent, a low pH detergent, or a compact detergent. In additional embodiments, the present invention provides methods for cleaning, comprising the step of contacting a surface and/or an article comprising a fabric with a cleaning composition comprising at least one subtilisin variant.

Cleaning Compositions

The cleaning compositions of the present invention are advantageously employed for example, in laundry applications. Indeed, due to the unique advantages of increased effectiveness in lower temperature solutions, the enzymes of the present invention are ideally suited for laundry applications. Furthermore, the enzymes of the present invention may be employed in both granular and liquid compositions.

The variant proteases of the present invention also find use laundry cleaning additive products. In some embodiments, low temperature solution cleaning applications find use. The additive product may be, in its simplest form, one or more proteases. In some embodiments, the additive is packaged in dosage form for addition to a cleaning process. Any suitable single dosage form also finds use with the present invention, including but not limited to pills, tablets, gelcaps, or other single dosage units such as pre-measured powders or liquids. In some embodiments, filler(s) or carrier material(s) are included to increase the volume of such composition. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, the cleaning additive includes adjunct ingredients as more fully described below.

The present cleaning compositions and cleaning additives require an effective amount of at least one of the protease variants provided herein, alone or in combination with other proteases and/or additional enzymes. The required level of enzyme is achieved by the addition of one or more protease variants of the present invention. Typically the present cleaning compositions comprise at least about 0.0001 weight percent, from about 0.0001 to about 1, from about 0.001 to about 0.5, or even from about 0.01 to about 0.1 weight percent of at least one of the variant proteases of the present invention.

The cleaning compositions herein are typically formulated such that, during use in aqueous cleaning operations, the wash water will have a pH of from about 5.0 to about 11.5 or even from about 7.5 to about 10.5. Liquid product formulations are typically formulated to have a neat pH from about 3.0 to about 9.0 or even from about 3 to about 5.

Granular laundry products are typically formulated to have a pH from about 9 to about 11. Techniques for controlling pH at recommended usage levels include the use of buffers, alkalis, acids, etc., and are well known to those skilled in the art.

Suitable low pH cleaning compositions typically have a neat pH of from about 3 to about 5, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a neat pH of from about 3 to about 5. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C.

In some embodiments, when the variant protease(s) is/are employed in a granular composition or liquid, it is desirable for the variant protease to be in the form of an encapsulated particle to protect the variant protease from other components of the granular composition during storage. In addition, encapsulation is also a means of controlling the availability of the variant protease during the cleaning process. In some embodiments, encapsulation enhances the performance of the variant protease(s) and/or additional enzymes. In this regard, the variant proteases of the present invention are encapsulated with any suitable encapsulating material known in the art. In some embodiments, the encapsulating material typically encapsulates at least part of the catalyst for the variant protease(s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. Typically, the encapsulating material is a starch. Suitable starches are described in EP 0 922 499; U.S. Pat. Nos. 4,977,252; 5,354,559, and 5,935,826. In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.)>

As described herein, the variant proteases of the present invention find particular use in laundry detergents. These applications place enzymes under various environmental stresses. The variant proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, a European detergent typically has about 4500-5000 ppm of detergent components in the wash water, while a Japanese detergent typically has approximately 667 ppm of detergent components in the wash water. In North America, particularly the United States, detergents typically have about 975 ppm of detergent components present in the wash water.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between 10 and 30° C. (e.g., about 20° C.), whereas the temperature of wash water in Europe is typically between 30 and 60° C. (e.g., about 40° C.).

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
| --- | --- | --- |
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than 10.5 (for example 10.5-20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between 3 to 10 grains, 3-8 grains or about 6 grains. Japanese water hardness is typically lower than North American water hardness, usually less than 4, for example 3 grains per gallon mixed $Ca^{2+}/Mg^{2+}$.

Accordingly, in some embodiments, the present invention provides variant proteases that show surprising wash performance in at least one set of wash conditions (e.g., water temperature, water hardness, and/or detergent concentration). In some embodiments, the variant proteases of the present invention are comparable in wash performance to other subtilisin proteases. In some embodiments, the variant proteases of the present invention exhibit enhanced wash performance as compared to subtilisin proteases currently commercially available. Thus, in some preferred embodiments of the present invention, the variant proteases provided herein exhibit enhanced oxidative stability, enhanced thermal stability, and/or enhanced chelator stability. In addition, the variant proteases of the present invention find use in cleaning compositions that do not include detergents, again either alone or in combination with builders and stabilizers.

In some embodiments of the present invention, the cleaning compositions comprise at least one variant protease of the present invention at a level from about 0.00001% to about 10% by weight of the composition and the balance (e.g., about 99.999% to about 90.0%) comprising cleaning adjunct materials by weight of composition. In other aspects of the present invention, the cleaning compositions of the present invention comprises at least one variant protease at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, preferred cleaning compositions comprise one or more additional enzymes or enzyme derivatives which provide cleaning performance and/or fabric care benefits, in addition to one or more of the variant proteases provided herein. Such enzymes include, but are not limited to other proteases, lipases, cutinases, amylases, cellulases, peroxidases, oxidases (e.g. laccases), and/or mannanases.

Any other suitable protease finds use in the compositions of the present invention. Suitable proteases include those of animal, vegetable or microbial origin. In some particularly preferred embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the *Fusarium* protease described in WO 89/06270. Preferred commercially available protease enzymes include MAXATASE®, MAXACAL™, MAXAPEM™, OPTICLEAN®, OPTIMASE®, PROPERASE®, PURAFECT® and PURAFECT® OXP (Genencor); ALCALASE®, SAVINASE®, PRIMASE®, DURAZYM™, RELASE® and ESPERASE® (Novozymes); and BLAP™ (Henkel Kommanditgesellschaft auf Aktien, Duesseldorf, Germany. Various proteases are described in WO95/23221, WO 92/21760, and U.S. Pat. Nos. 5,801,039, 5,340,735, 5,500,364, 5,855,625, US RE 34,606, 5,955,340, 5,700,676, 6,312,936, and 6,482,628, and various other patents.

In addition, any suitable lipase finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), a *Pseudomonas* lipase such as *P. alcaligenes* and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipolytic enzymes such as cutinases also find use in some embodiments of the present invention, including but not limited to the cutinase derived from *Pseudomonas mendocina* (See, WO 88/09367), and the cutinase derived from *Fusarium solani pisi* (See, WO 90/09446).

Additional suitable lipases include commercially available lipases such as M1 LIPASE™, LUMA FAST™, and LIPOMAX™ (Genencor); LIPOLASE® and LIPOLASE®

ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In other aspects of the present invention, the cleaning compositions of the present invention also comprise, lipases at a level of about 0.0001% to about 10%, about 0.001% to about 5%, about 0.001% to about 2%, about 0.005% to about 0.5% lipase by weight of the composition.

Any amylase (alpha and/or beta) suitable for use in alkaline solutions also find use in some embodiments of the present invention. Suitable amylases include, but are not limited to those of bacterial or fungal origin. Chemically or genetically modified mutants are included in some embodiments. Amylases that find use in the present invention, include, but are not limited to a-amylases obtained from *B. licheniformis* (See e.g., GB 1,296,839). Commercially available amylases that find use in the present invention include, but are not limited to DURAMYL®, TERMAMYL®, FUNGAMYL® and BAN™ (Novozymes) and RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In other aspects of the present invention, the cleaning compositions of the present invention also comprise, amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME® (Novozymes), and KAC-500 (B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276). In some embodiments, the cleaning compositions of the present invention further comprise cellulases at a level from about 0.00001% to about 10% of additional cellulase by weight of the composition and the balance of cleaning adjunct materials by weight of composition. In other aspects of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114, 6,602,842, and 6,440,991, all of which are incorporated herein by reference). In some embodiments, the cleaning compositions of the present invention further comprise mannanases at a level from about 0.00001% to about 10% of additional mannanase by weight of the composition and the balance of cleaning adjunct materials by weight of composition. In other aspects of the present invention, the cleaning compositions of the present invention also comprise, mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In other aspects of the present invention, the cleaning compositions of the present invention also comprise peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some particularly preferred embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the variant protease(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

By way of example, several cleaning compositions wherein the variant proteases of the present invention find use are described in greater detail below. In embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In some embodiments, various cleaning compositions such as those provided in U.S. Pat. No. 6,605,458 find use with the variant proteases of the present invention. Thus, in some embodiments, the compositions comprising at least one variant protease of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one variant protease of the present invention are fabric cleaning compositions such as those described in U.S. Pat. Nos. 6,610,642 and 6,376,450. In addition, the variant proteases of the present invention find use in granular laundry detergent compositions of particular utility under European or Japanese washing conditions (See e.g., U.S. Pat. No. 6,610,642).

The cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition is adjusted via the addition of a material such as monoethanolamine or an acidic material such as HCl.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the variant proteases of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/ or pigments. In addition to the disclosure below, suitable examples of such other adjuncts and levels of use are found in U.S. Pat. Nos. 5,576,282, 6,306,812, and 6,326,348, that are incorporated by reference. The aforementioned adjunct ingredients may constitute the balance of the cleaning compositions of the present invention.

In some embodiments, the cleaning compositions according to the present invention comprise a surfactant or surfactant system wherein the surfactant is selected from nonionic surfactants, anionic surfactants, cationic surfactants, ampholytic surfactants, zwitterionic surfactants, semi-polar nonionic surfactants and mixtures thereof.

In some additional embodiments, the cleaning compositions of the present invention comprise one or more detergent builders or builder systems. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

In some further embodiments, the cleaning compositions herein contain a chelating agent. Suitable chelating agents include copper, iron and/or manganese chelating agents and mixtures thereof.

In some still further embodiments, the cleaning compositions provided herein contain a deposition aid. Suitable deposition aids include, polyethylene glycol, polypropylene glycol, polycarboxylate, soil release polymers such as polytelephthalic acid, clays such as Kaolinite, montmorillonite, atapulgite, illite, bentonite, halloysite, and mixtures thereof.

In some additional embodiments, the cleaning compositions of the present invention also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

In some still additional embodiments, the cleaning compositions of the present invention also contain dispersants. Suitable water-soluble organic materials include the homoor co-polymeric acids or their salts, in which the polycarboxylic acid comprises at least two carboxyl radicals separated from each other by not more than two carbon atoms.

In some particularly preferred embodiments, the cleaning compositions comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes including at least one protease, at least one lipase, at least one cutinase, and/or at least one cellulase in conjunction with at least one amylase.

In some further embodiments, the enzymes used in the cleaning compositions are stabilized any suitable technique. In some embodiments, the enzymes employed herein are stabilized by the presence of water-soluble sources of calcium and/or magnesium ions in the finished compositions that provide such ions to the enzymes.

In some still further embodiments, the cleaning compositions of the present invention include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

In some embodiments, the compositions herein are catalyzed by means of a manganese compound. Such compounds and levels of use are well known in the art and include, for example, the manganese-based catalysts disclosed in U.S. Pat. No. 5,576,282. In addition, cobalt bleach catalysts useful herein are known, and are described, for example, in U.S. Pat. Nos. 5,597,936, and 5,595,967. Such cobalt catalysts are readily prepared by known procedures, such as taught for example in U.S. Pat. Nos. 5,597,936, and 5,595,967. In some embodiments, the compositions provided herein also suitably include a transition metal complex of a macropolycyclic rigid ligand (i.e., "MRL"). As a practical matter, and not by way of limitation, the compositions and cleaning processes herein are adjustable, to provide on the order of at least one part per hundred million of the active MRL species in the aqueous washing medium, and will preferably provide from about 0.005 ppm to about 25 ppm, more preferably from about 0.05 ppm to about 10 ppm, and most preferably from about 0.1 ppm to about 5 ppm, of the MRL in the wash liquor. Preferred transition-metals in the instant transition-metal bleach catalyst include manganese, iron and chromium. Preferred MRLs herein are a special type of ultra-rigid ligand that is cross-bridged such as 5,12-diethyl-1,5,8,12-tetraazabicyclo[6.6.2]hexadecane. Suitable transition metal MRLs are readily prepared by known procedures, such as taught for example in WO 00/332601, and U.S. Pat. No. 6,225,464.

As indicated above, the cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,516,448, 5,489,392, and 5,486,303, all of which are incorporated herein by reference.

The cleaning compositions disclosed herein of find use in cleaning a situs (e.g., a surface, dishware, or fabric). Typically, at least a portion of the situs is contacted with an embodiment of the present cleaning composition, in neat form or diluted in a wash liquor, and then the situs is optionally washed and/or rinsed. For purposes of the present invention, "washing" includes but is not limited to, scrubbing, and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

Definitions

Unless otherwise indicated, the practice of the present invention involves conventional techniques commonly used in molecular biology, protein engineering, microbiology, and recombinant DNA, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. There are various dictionaries available and known to those in the art that provide definitions of these terms. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the respective protease's ability to hydrolyze a commercial substrate. Exemplary substrates useful in the analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference). The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and nucleotide branches. In alternative embodiments, the sequence of nucleotides is interrupted by non-nucleotide components.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks) In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell, and/or 2) mutagenize a region of the host cell chromosome (i.e., replace an endogenous sequence with a heterologous sequence), 3) delete target genes, and/or 4) introduce a replicating plasmid into the host.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the protease (e.g., precursor or mature protease) that is operably linked to a suitable prosequence (e.g., secretory, etc.) capable of effecting the expression of the DNA in a suitable host.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "*Genetics*," in Hardwood et al, (eds.), *Bacillus*, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, proteins are defined as having a common "fold" if they have the same major secondary structures in the same arrangement and with the same topological connections. Different proteins with the same fold often have peripheral elements of secondary structure and turn regions that differ in size and conformation. In some cases, these differing peripheral regions may comprise half the structure. Proteins placed together in the same fold category do not necessarily have a common evolutionary origin (e.g., structural similarities arising from the physics and chemistry of proteins favoring certain packing arrangements and chain topologies).

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene based on the wild-type subtilisin protease. Additionally, analogous genes include at least about 45%, about 50%, about 55%, about 60%, about 65%, about 70%, about 75%, about 80%, about 85%, about 90%, about 95%, about 97%, about 98%, about 99%, or about 100% sequence identity with the sequence of the wild-type subtilisin protease. Alternately, analogous sequences have an alignment of between about 70 to about 100% of the genes found in the *B. amyloliquefaciens* subtilisin protease region. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In some preferred embodiments, mutant DNA sequences are generated with site saturation mutagenesis in at least one codon. In another preferred embodiment, site saturation mutagenesis is performed for two or more codons. In a further embodiment, mutant DNA sequences have more than about 50%, more than about 55%, more than about 60%, more than about 65%, more than about 70%, more than about 75%, more than about 80%, more than about 85%, more than about 90%, more than about 95%, or more than about 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhabitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

"Homologous recombination" means the exchange of DNA fragments between two DNA molecules or paired chromosomes at the site of identical or nearly identical nucleotide sequences. In a preferred embodiment, chromosomal integration is homologous recombination.

As used herein "amino acid" refers to peptide or protein sequences or portions thereof. The terms "protein," "peptide," and "polypeptide" are used interchangeably.

As used herein, "protein of interest" and "polypeptide of interest" refer to a protein/polypeptide that is desired and/or being assessed. In some embodiments, the protein of interest is expressed intracellularly, while in other embodiments, it is a secreted polypeptide. In particularly preferred embodiments, these enzymes include the serine proteases of the present invention. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

A polynucleotide is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences. As is known in the art, a DNA can be transcribed by an RNA polymerase to produce RNA, but an RNA can be reverse transcribed by reverse transcriptase to produce a DNA. Thus a DNA can encode a RNA and vice versa.

"Host strain" or "host cell" refers to a suitable host for an expression vector comprising DNA according to the present invention.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used throughout this disclosure. It is also understood that a polypeptide may be coded for by more than one nucleotide sequence due to the degeneracy of the genetic code.

A "prosequence" is an amino acid sequence between the signal sequence and mature protease that is necessary for the secretion of the protease. Cleavage of the pro sequence results in a mature active protease.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536).

The term "hybrid signal sequence" refers to signal sequences in which part of sequence is obtained from the expression host fused to the signal sequence of the gene to be expressed. In some embodiments, synthetic sequences are utilized.

The term "mature" form of a protein or peptide refers to the final functional form of the protein or peptide. For example, the mature form of the BPN' subtilisin protease of the present invention includes at least the amino acid sequence identical to residue positions 1-275 of SEQ ID NO:1, as set forth below:

```
                                         (SEQ ID NO: 1)
AQSVPYGVSQIKAPALHSQGYTGSNVKVAVIDSGIDSSHPDLKVAGG

ASMVPSETNPFQDNNSHGTHVAGTVAALNNSIGVLGVAPSASLYAVK

VLGADGSGQYSWIINGIEWAIANNMDVINMSLGGPSGSAALKAAVDK

AVASGVVVVAAAGNEGTSGSSSTVGYPGKYPSVIAVGAVDSSNQRAS

FSSVGPELDVMAPGVSIQSTLPGNKYGAYNGTSMASPHVAGAAALIL

SKHPNWTNTQVRSSLENTTTKLGDSFYYGKGLINVQAAAQ
```

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question.

A "derivative" within the scope of this definition generally retains the characteristic proteolytic activity observed in the wild-type, native or parent form to the extent that the derivative is useful for similar purposes as the wild-type, native or parent form. Functional derivatives of serine protease encompass naturally occurring, synthetically or recombinantly produced peptides or peptide fragments which have the general characteristics of the serine protease of the present invention.

The term "functional derivative" refers to a derivative of a nucleic acid which has the functional characteristics of a nucleic acid which encodes serine protease. Functional derivatives of a nucleic acid which encode serine protease of the present invention encompass naturally occurring, synthetically or recombinantly produced nucleic acids or fragments and encode serine protease characteristic of the present invention. Wild type nucleic acid encoding serine proteases according to the invention include naturally occurring alleles and homologues based on the degeneracy of the genetic code known in the art.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucleotide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least about 70% sequence identity, preferably at least about 75%, preferably at least about 80%, preferably at least about 85%, preferably at least about 90%, preferably at least about 95%, preferably at least about 97%, preferably at least about 98%, and preferably at least about 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The phrase "equivalent" in this context, refers to serine proteases enzymes that are encoded by a polynucleotide capable of hybridizing to the polynucleotide encoding the protease of interest, under conditions of medium to maximum stringency. For example, being equivalent means that an equivalent mature serine protease comprises at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, and/or at least about 99% sequence identity to the mature subtilisin protease having the amino acid sequence of SEQ ID NO:1.

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78 [1985]). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. An isolated protein is more than about 10% pure, preferably more than about 20% pure, and even more preferably more than about 30% pure, as determined by SDS-PAGE. Further aspects of the invention encompass the protein in a highly purified form (i.e., more than about 40% pure, more than about 60% pure, more than about 80% pure, more than about 90% pure, more than about 95% pure, more than about 97% pure, and even more than about 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations which were not members of the predefined set of mutations. In some embodiments, the methods include those set forth in U.S. patent application Ser. No. 09/699,250, filed Oct. 26, 2000, hereby incorporated by reference. In alternative embodiments, combinatorial mutagenesis methods encompass commercially available kits (e.g., QuikChange® Multisite, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein, the term "starting gene" refers to a gene of interest that encodes a protein of interest that is to be improved and/or changed using the present invention.

As used herein, the term "multiple sequence alignment" ("MSA") refers to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence resulting from an MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

As used herein, the term "enhanced combinatorial consensus mutagenesis library" refers to a CCM library that is designed and constructed based on screening and/or sequencing results from an earlier round of CCM mutagenesis and screening. In some embodiments, the enhanced CCM library is based on the sequence of an initial hit resulting from an earlier round of CCM. In additional embodiments, the enhanced CCM is designed such that mutations that were frequently observed in initial hits from earlier rounds of mutagenesis and screening are favored. In some preferred embodiments, this is accomplished by omitting primers that encode performance-reducing mutations or by increasing the concentration of primers that encode performance-enhancing mutations relative to other primers that were used in earlier CCM libraries.

As used herein, the term "performance-reducing mutations" refer to mutations in the combinatorial consensus mutagenesis library that are less frequently found in hits resulting from screening as compared to an unscreened combinatorial consensus mutagenesis library. In preferred embodiments, the screening process removes and/or reduces the abundance of variants that contain "performance-reducing mutations."

As used herein, the term "functional assay" refers to an assay that provides an indication of a protein's activity. In particularly preferred embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some preferred embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide (including proteins), as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, $K_M$, $k_{cat}$, $k_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced enzymatic activity).

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or "non-mutagenic oligonucleotide" refers to oligonucleotide compositions which will match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their precursor sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10-50 bases in length, more preferably about 15-45 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added. Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

As used herein, the phrase "contiguous mutations" refers to mutations which are presented within the same oligonucleotide primer. For example, contiguous mutations may be adjacent or nearby each other, however, they will be introduced into the resulting mutant template nucleic acids by the same primer.

The terms "wild-type sequence," or "wild-type gene" are used interchangeably herein, to refer to a sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for the intervention. Unless otherwise indicated, the amino acid position numbers refer to those assigned to the mature *Bacillus amyloliquefaciens* subtilisin sequence of SEQ ID NO:1. The invention, however, is not limited to the mutation of this particular subtilisin but extends to precursor proteases containing amino acid residues at positions which are "equivalent" to the particular identified residues in the *Bacillus amyloliquefaciens* subtilisin.

As used herein, the terms "protease variant," "subtilisin variant," "subtilisin protease variant," are used in reference to proteases that are similar to a wild-type subtilisin or a parent protease (e.g., subtilisin) used as a starting point in protein engineering. These variants are similar to the wild-type or other parent in their function, but have mutations in their amino acid sequence that make them different in sequence from the wild-type or parent protease (e.g., subtilisin).

As used herein, the terms "modification" and "mutation" refers to any change or alteration in an amino acid sequence. It is intended that the term encompass substitutions, deletions, insertions, and/or replacement of amino acid side chains in an amino acid sequence of interest (e.g., a subtilisin sequence). It is also intended that the term encompass chemical modification of an amino acid sequence of interest (e.g., a subtilisin sequence).

The term "oxidation stable" refers to proteases of the present invention that retain a specified amount of enzymatic activity over a given period of time under conditions prevailing during the proteolytic, hydrolyzing, cleaning or other process of the invention, for example while exposed to or contacted with bleaching agents or oxidizing agents. In some embodiments, the proteases retain at least about 50%, about 60%, about 70%, about 75%, about 80%, about 85%, about 90%, about 92%, about 95%, about 96%, about 97%, about 98%, or about 99% proteolytic activity after contact with a bleaching or oxidizing agent over a given time period, for example, at least about 1 minute, about 3 minutes, about 5 minutes, about 8 minutes, about 12 minutes, about 16 minutes, about 20 minutes, etc. In some embodiments, the stability is measured as described in the Examples.

The term "chelator stable" refers to proteases of the present invention that retain a specified amount of enzymatic activity over a given period of time under conditions prevailing during the proteolytic, hydrolyzing, cleaning or other process of the invention, for example while exposed to or contacted with chelating agents. In some embodiments, the proteases retain at least about 50%, about 60%, about 70%, about 75%, about 80%, about 85%, about 90%, about 92%, about 95%, about 96%, about 97%, about 98%, or about 99% proteolytic activity after contact with a chelating agent over a given time period, for example, at least about 10 minutes, about 20 minutes, about 40 minutes, about 60 minutes, about 100 minutes, etc. In some embodiments, the chelator stability is measured as described in the Examples.

The terms "thermally stable" and "thermostable" refer to proteases of the present invention that retain a specified amount of enzymatic activity after exposure to identified temperatures over a given period of time under conditions prevailing during the proteolytic, hydrolyzing, cleaning or other process of the invention, for example while exposed altered temperatures. Altered temperatures include increased or decreased temperatures. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to altered temperatures over a given time period, for example, at least about 60 minutes, about 120 minutes, about 180 minutes, about 240 minutes, about 300 minutes, etc. In some embodiments, the thermostability is determined as described in the Examples.

The term "enhanced stability" in the context of an oxidation, chelator, thermal and/or pH stable protease refers to a higher retained proteolytic activity over time as compared to other serine proteases (e.g., subtilisin proteases) and/or wild-type enzymes.

The term "diminished stability" in the context of an oxidation, chelator, thermal and/or pH stable protease refers to a lower retained proteolytic activity over time as compared to other serine proteases (e.g., subtilisin proteases) and/or wild-type enzymes.

The term "cleaning activity" refers to the cleaning performance achieved by the protease under conditions prevailing during the proteolytic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the Examples.

As used herein, "cleaning compositions" and "cleaning formulations" refer to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, or spray composition), as long as the composition is compatible with the perhydrolase and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some preferred embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that in addition to perhydrolase, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

The term "cleaning effective amount" of a protease refers to the quantity of protease described hereinbefore that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, bar) composition is required, etc.

The term "cleaning adjunct materials," as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the protease enzyme used in the composition. In some embodiments, granular compositions are in "compact" form, while in other embodiments, the liquid compositions are in a "concentrated" form.

The term "enhanced performance" in the context of cleaning activity refers to an increased or greater cleaning activity of certain enzyme sensitive stains such as egg, milk, grass or blood, as determined by usual evaluation after a standard wash cycle and/or multiple wash cycles.

The term "diminished performance" in the context of cleaning activity refers to an decreased or lesser cleaning activity of certain enzyme sensitive stains such as egg, milk, grass or blood, as determined by usual evaluation after a standard wash cycle.

The term "comparative performance" in the context of cleaning activity refers to at least about 60%, at least about 70%, at least about 80% at least about 90%, or at least about 95% of the cleaning activity of a comparative subtilisin protease (e.g., commercially available proteases), including but not limited to OPTIMASE™ protease (Genencor), PURAFECT™ protease products (Genencor), SAVINASE™ protease (Novozymes), BPN'-variants (See e.g., U.S. Pat. No. Re 34,606), RELASE™, DURAZYME™, EVERLASE™, KANNASE™ protease (Novozymes), MAXACAL™, MAXAPEM™, PROPERASE™ proteases (Genencor; See also, U.S. Pat. No. Re 34,606, and U.S. Pat. Nos. 5,700,676; 5,955,340; 6,312,936; and 6,482,628), and B. lentus variant protease products (e.g., those described in WO 92/21760, WO 95/23221 and/or WO 97/07770). Exemplary subtilisin protease variants include, but are not limited to those having substitutions or deletions at residue positions equivalent to positions 76, 101, 103, 104, 120, 159, 167, 170, 194, 195, 217, 232, 235, 236, 245, 248, and/or 252 of BPN'. Cleaning performance can be determined by comparing the proteases of the present invention with those subtilisin proteases in various cleaning assays concerning enzyme sensitive stains such as grass, blood or milk as determined by usual spectrophotometric or analytical methodologies after standard wash cycle conditions.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. A preferred filler salt is sodium sulfate.

As used herein, the term "surfactant" refers to any compound generally recognized in the art as having surface active qualities. Surfactants generally include anionic, cationic, nonionic, and zwitterionic compounds, which are further described, herein.

EXPERIMENTAL

The present invention is described in further detail in the following Examples which are not in any way intended to limit the scope of the invention as claimed. The following Examples are offered to illustrate, but not to limit the claimed invention.

In the experimental disclosure which follows, the following abbreviations apply: PI (proteinase inhibitor), ppm (parts per million); M (molar); mM (millimolar); µM (micromolar); nM (nanomolar); mol (moles); mmol (millimoles);

μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/1$K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN® 20); PEG (polyethylene glycol); PCR (polymerase chain reaction); RT-PCR (reverse transcription PCR); SDS (sodium dodecyl sulfate); Tris (tris (hydroxymethyl)aminomethane); HEPES (N-[2-Hydroxyethyl]piperazine-N-[2-ethanesulfonic acid]); HBS (HEPES buffered saline); Tris-HCl (tris[Hydroxymethyl]aminomethane-hydrochloride); Tricine (N-[tris-(hydroxymethyl)-methyl]glycine); CHES (2-(N-cyclo-hexylamino) ethanesulfonic acid); TAPS (3-{[tris-(hydroxymethyl)-methyl]-amino}-propanesulfonic acid); CAPS (3-(cyclohexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl]phosphine); Ci (Curies); mCi (milliCuries); μCi (microCuries); HPLC (high pressure liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); EGTA (ethylene glycol-bis(β-aminoethyl ether) N,N,N',N'-tetraacetic acid); EDTA (ethylenediaminetetracetic acid); bla (β-lactamase or ampicillin-resistance gene); HDL (high density liquid); MJ Research (MJ Research, Reno, Nev.); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y.); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, the Netherlands); Test Fabrics (Test Fabrics, Inc., West Pittiston, Pa.), Procter & Gamble (Procter & Gamble, Inc., Cincinnati, Ohio); GE Healthcare (GE Healthcare, Chalfont St. Giles, United Kingdom); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc, King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Ipswich, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); United States Testing (United States Testing Co., Hoboken, N.J.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Geneart (Geneart GmbH, Regensburg, Germany); DNA2.0 (DNA2.0, Menlo Park, Calif.); Gene Oracle (Gene Oracle, Mountain View, Calif.); Bio-Tek (Bio-Tek Instruments, Winooski, Vt.); Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Enichem (Enichem Iberica, Barcelona, Spain); Fluka Chemie AG (Fluka Chemie AG, Buchs, Switzerland); Gist-Brocades (Gist-Brocades, NV, Delft, the Netherlands); Dow Corning (Dow Corning Corp., Midland, Mich.); and Microsoft (Microsoft, Inc., Redmond, Wash.).

Example 1

Assays

In the following Examples, various assays were used as set forth below for ease in reading. Any deviations from the protocols provided below are indicated in the Examples.

A. TCA Assay for Protein Content Determination in 96-Well Microtiter Plates

For BPN' (e.g., reference protease) and BPN' variants, this assay was started using filtered culture supernatant from microtiter plates grown 3-4 days at 33° C. with shaking at 230 rpm and humidified aeration. A fresh 96-well flat bottom microtiter plate (MTP) was used for the assay. First, 100 µL/well of 0.25 N HCl was placed in each well. Then, 50 µL of filtered culture broth was added. The light scattering/absorbance at 405 nm (use 5 sec mixing mode in the plate reader) was then determined, in order to provide the "blank" reading. For the test, 100 µL/well of 15% (w/v) trichloroacetic acid (TCA) was placed in the plates and incubated between 5 and 30 min at room temperature. The light scattering/absorbance at 405 nm (use 5 sec mixing mode in the plate reader) was then determined The equipment used was a Biomek FX Robot (Beckman Coulter) and a SpectraMAX (type 340; Molecular Devices) MTP Reader; the MTP's were from Costar (type 9017). The equipment used was a Biomek FX Robot (Beckman Coulter) and a SpectraMAX type 340 (Molecular Devices) MTP Reader; and the MTPs were type 9017 (Costar).

The calculations were performed by subtracting the blank (no TCA) from the test reading with TCA to provide a relative measure of the protein content in the samples. If desired, a standard curve can be created by calibrating the TCA readings with AAPF assays of clones with known conversion factors. However, the TCA results are linear with respect to protein concentration from 50 to 500 protein per ml (ppm) and can thus be plotted directly against enzyme performance for the purpose of choosing good-performing variants. The turbidity/light scatter increase in the samples correlates to the total amount of precipitable protein in the culture supernatant.

B. AAPF Protease Assay in 96-Well Microtiter Plates

In order to determine the protease activity of the proteases and variants thereof of the present invention, the hydrolysis of N-succinyl-L-alanyl-L-alanyl-L-prolyl-L-phenyl-p-nitroanilide (suc-AAPF-pNA) (SEQ ID NO: 2) was measured. The reagent solutions used were: 100 mM Tris/HCl, pH 8.6, containing 0.005% TWEEN®-80 (Tris dilution buffer); 100 mM Tris buffer, pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 µl of diluted protease solution to each well, immediately followed by the addition of 190 µl 1 mg/ml suc-AAPF-pNA working solution. The solutions were mixed for 5 sec., and the absorbance change in kinetic mode (20 readings in 5 minutes) was read at 410 nm in an MTP reader, at 25° C. The protease activity was expressed as AU (activity=$\Delta$OD·min$^{-1}$ ml$^{-1}$).

C. Surfactant and Chelant Stability Assays

LAS and LAS/EDTA stability was measured after incubation of the test protease in the presence of LAS and LAS/EDTA respectively, as a function of residual activity determined using the AAPF assay.

LAS Stability Method
Reagents:
Dodecylbenzenesulfonate, Sodium salt (=LAS): Sigma D-2525
TWEEN®-80: Sigma P-8074
TRIS buffer (free acid): Sigma T-1378); 6.35 g is dissolved in about 960 ml water; pH is adjusted to 8.2 with 4N HCl. Final concentration of TRIS is 52.5 mM.

LAS stock solution: Prepare a 10.5% LAS solution in MQ water (=10.5 g per 100 ml MQ)
TRIS buffer-100 mM/pH 8.6 (100 mM Tris/0.005% Tween®-80)
TRIS-Ca buffer, pH 8.6 (100 mM Tris/10 mM CaCl2/0.005% Tween-®80)
Hardware:
Flat bottom MTPs (Costar No. 9017)
Biomek FX
ASYS Multipipettor
Spectramax MTP Reader
iEMS Incubator/Shaker
Innova 4330 Incubator/Shaker
Biohit multichannel pipette
BMG Thermostar Shaker A 0.063% LAS solution was prepared in 52.5 mM Tris buffer pH 8.2. The suc-AAPF-pNA working solution was prepared by adding 1 ml of 100 mg/ml suc-AAPF-pNA stock solution (in DMSO) to 100 ml (100 mM) TRIS buffer, pH 8.6. To dilute the supernatants, flat-bottomed plates were filled with dilution buffer and an aliquot of the supernatant was added and mixed well. The dilution ratio depended on the concentration of the protease controls in the growth plates (AAPF activity). The desired protein concentration was 80 ppm.

Ten µl of the diluted supernatant were added to 190 µl 0.063% LAS buffer/well. The MTP was covered with tape, shaken for a few seconds and placed in an incubator (Innova 4230) at 45° C., for 60 minutes at 200 rpm agitation. The initial activity (t=10 minutes) was determined after 10 minutes of incubation by transferring 10 µl of the mixture in each well to a fresh MTP containing 190 µl suc-AAPF-pNA work solution. These solutions were mixed well and the AAPF activity was measured using a MTP Reader (20 readings in 5 minutes and 25° C.).

The final activity (t=60 minutes) was determined by removing another 10 µl of solution from the incubating plate after 60 minutes of incubation. The AAPF activity was then determined as described above. The stability of the samples was determined by calculating the ration of the residual and initial AAPF activity as follows:

$$\text{Residual Activity (\%)} = [t\text{–}60 \text{ value}]*100/[t\text{–}10 \text{ value}].$$

LAS/EDTA Stability Method

The stability of protease variants in the presence of a representative anionic surfactant (LAS=linear alkylbene sulfonate, sodium dodecylbenzenesulfonate-DOBS) and di-sodium EDTA was measured after incubation under defined conditions and the residual activity was determined using the AAPF assay. The reagents used were dodecyllbenzene sulfonate, sodium salt (DOBS, Sigma No. D-2525), TWEEN®-80 (Sigma No. P-8074), di-sodium EDTA (Siegfried Handel No. 164599-02), HEPES (Sigma No. H-7523), unstress buffer: 50 mM HEPES (11.9 g/l)+0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 µg/ml protein. The equipment used was V- or U-bottom MTP as dilution plates (Greiner 651101 and 650161 respectively), F-bottom MTP (Corning 9017) for unstress and LAS/EDTA buffer as well as for suc-AAPF-pNA plates, Biomek FX (Beckman Coulter), Spectramax Plus 384 MTP Reader (Molecular Devices), iEMS Incubator/Shaker (1 mm amplitude) (Thermo Electron Corporation), sealing tape: Nunc (236366)

The iEMS incubator/shaker (Thermo/Labsystems) was set at 29° C. Culture supernatants were diluted into plates containing unstress buffer to a concentration of 25 ppm (master dilution plate). 20 µl of sample from the master dilution plate was added to plates containing 180 µl unstress buffer to give a final incubation concentration of 2.5 ppm. The contents were mixed and kept at room temperature and a AAPF assay was performed on this plate. 20 µl of sample from the master dilution plate was also added to plates containing 180 µl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 min at 400 rpm. Following 30 minutes of incubation, a AAPF assay was performed on the stress plate. The stability of the samples was determined by calculating the ration of the residual and initial AAPF activity as follows: Residual Activity (%)=[mOD·min−1 stressed]*100/[mOD·min−1 unstressed].

D. Cleaning Performance Assays

The stain removal performance of the protease variants was determined in commercially available detergents. Heat inactivation of commercial detergent formulas serves to destroy the enzymatic activity of any protein components while retaining the properties of non-enzymatic components. Thus this method was suitable for preparing commercially purchased detergents for use in testing the enzyme variants of the present invention.

Microswatches:

Microswatches of ¼" circular diameter were ordered and delivered by CFT (Vlaardingen, The Netherlands). Single microswatches or two microswatches were placed vertically in each well of a 96-well MTP to expose the whole surface area (i.e., not flat on the bottom of the well).

BMI Microswatch Assay

Microswatches containing blood milk and ink (BMI) of 0.25 inch circular diameter were obtained from CFT. Before cutting of the swatches, the fabric (EMPA 116) was washed with water. One microswatch was vertically placed in each well of a 96-well microtiter plate in order to expose the whole surface area (i.e., not flat on the bottom of the well). The desired detergent solution was prepared as described herein. After equilibrating the Thermomixer at 25° C., 190 µl of detergent solution was added to each well of the MTP, containing microswatches. To this mixture, 10 µl of the diluted enzyme solution was added so that the final enzyme concentration was 1 µg/ml (determined from BCA assay). The MTP was sealed with tape and placed in the incubator for 30 minutes, with agitation at 1400 rpm. Following incubation under the appropriate conditions, 100 µl of the solution from each well was transferred into a fresh MTP. The new MTP containing 100 µl of solution/well was read at 405 nm using a MTP SpectraMax reader. Blank controls, as well as a control containing two microswatches and detergent but no enzyme were also included.

"Pre-Washed" Swatch

This type of microswatch was pre-washed in deionised water for 20 minutes at ambient temperature. After the pre-washing step, the swatches were put on top of paper towels to dry. The air-dried swatches were then punched using a ¼" circular die on an expulsion press. Finally two microswatches were put into each well of a 96-well MTP vertically to expose the whole surface area (i.e. not flat on the bottom of the well).

Detergents

For North American (NA) and Western European (WE) heavy duty liquid laundry (HDL) detergents, heat inactivation was performed by placing pre-weighed liquid detergent (in a glass bottle) in a water bath at 95° C. for 2 hours. The detergents were purchased from local supermarket stores. Both un-heated and heated detergents were assayed within 5 minutes of dissolving the detergent to accurately determine percentage deactivated. Enzyme activity was tested by the AAPF assay.

For testing of enzyme activity in heat-inactivated detergents, working solutions of detergents were made from the heat inactivated stocks. Appropriate amounts of water hardness (6 gpg) and buffer were added to the detergent solutions to match the desired conditions. The solutions were mixed by vortexing or inverting the bottles.

Enzymes and Equipment

Samples of reference serine proteases variants thereof were obtained from filtered culture broth of cultures grown in MTP plates. The equipment used was a Biomek FX Robot (Beckman Coulter), a SpectraMAX MTP Reader (type 340; Molecular Devices), an iEMS incubator/shaker (Thermo/Labsystems); F-bottom MTPs (Costar type 9017 used for reading reaction plates after incubation); and V-bottom MTPs (Greiner 651101 used for pre-dilution of supernatant). In this assay, the proteases hydrolyze the substrate and liberate pigment and insoluble particles from the substrate. Thus the rate of turbidity is a measure of enzyme activity.

The stain removal performance of reference serine proteases and variants therefrom on microswatches was determined on a MTP scale in commercially available heat-inactivated detergent. The reagents used were: 5 mM HEPES, pH 8.0 or 5 mM MOPS, pH 7 buffer, 3:1 Ca: Mg for medium water hardness. ($CaCl_2$: $MgCl2.6H2O$); 15000 grains per gallon (gpg) stock diluted to 6 gpg, 2 BMI (blood/milk/ink) swatches per plate: EMPA-116 BMI cotton swatches processed by CFT: pre-rinsed and punched 2 swatches per well, and heat inactivated TIDE® 2× Cold off-the-shelf detergent in which lack of protease activity was confirmed.

TABLE 1-2

Working Detergent Solutions

| Detergent | Temp (C.) | Detergent g/L | pH | Buffer | gpg | Protease |
|---|---|---|---|---|---|---|
| TIDE ® 2X Cold | 16 | 0.98 | 8 | 5 mM HEPES | 6 | BPN' |
| TIDE ® 2X Cold | 32 | 0.98 | 8 | 5 mM HEPES | 6 | BPN' |
| TIDE ® 2X Cold | 16 | 0.98 | 7 | 5 mM MOPS | 6 | BPN' |

The incubator was set at the desired temperature (16° C. or 32° C.). 10 µL samples from the master dilution plate of ~10 ppm enzyme was added to BMI 2-swatch plates with 190 µL working detergent solutions listed above. The volume was adjusted to give final concentration of 0.5 ppm for variants in the assay plates. The plates were immediately transferred to iEMS incubators and incubated for 30 minutes with 1400 rpm shaking at given temperature. Following incubation, 100 µL of supernatant was transferred into a new 96-well plate and the absorbance was measured in MTP Reader at 405 nm and/or 600 nm. Control wells, containing 1 or 2 microswatches and detergent without the addition of protease samples were also included in the test. The measurement at 405 nm provides a higher value and tracks pigment removal, while the measurement at 600 nm tracks turbidity and cleaning.

Calculation of the Stain Removal Activity for all Microswatch Assay Methods:

The absorbance value obtained was corrected for the blank value (substrate without enzyme), providing a measure of hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme.

E. Relative Specific Activity of Proteases and Variants Thereof

In order to discriminate the protease variants, the relative specific activity was calculated using suc-AAPF-pNA as a substrate, which enabled the comparison and ranking of the variants versus the wild-type or standard protease. The specific activity on the suc-AAPF-pNA substrate was determined by dividing the proteolytic activity by the measured TCA-values of each sample, using the assays described above. Using these values, the relative specific activity was calculated (specific activity of variant/specific activity of reference protease).

F. Performance Index

The performance index compares the performance of the variant (actual value) and the standard or reference protease (theoretical value) at the same protein concentration. In addition, the theoretical values can be calculated, using the parameters of the binding curve (i.e., Langmuir equation) of the standard protease. A performance index (PI) that is greater than 1 (PI>1) identifies a better variant as compared to the standard (e.g., wild-type), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

Example 2

Stain Removal Performance of BPN' Multiple Mutation Library (MML) Variants

BPN' multiple mutation libraries (or combinatorial libraries) were produced by Geneart or DNA 2.0, using BPN' as the parent protein. Protein concentration of culture supernatants was determined by TCA precipitation as described in Example 1. The stain removal performance of the variants was tested in laundry applications on EMPA 116 swatches (BMI stain, CFT) at pH 8/16° C., pH 7/16° C. and pH 8/32° C. using methods described in Example 1, with the following modifications. The test detergent used was heat inactivated TIDE® 2× Cold detergent (Procter & Gamble), prepared as described in Example 1. Heat inactivation of commercial detergent formulas serves to destroy the endogenous enzymatic activity of any protein components while retaining the properties of non-enzymatic components.

Heat inactivation of the detergents was performed by placing pre-weighed amounts of liquid detergent (in a glass bottle) in a water bath at 95° C. for 2 hours. The detergent was purchased from local supermarket stores. Both unheated and heated detergents were assayed within 5 minutes of dissolving the detergent, in order to accurately determine percentage deactivated. Enzyme activity was tested by AAPF assay. Functionality of BPN' variants was quantified as a performance index (Pi) (i.e., the ratio of performance of a variant relative to parent BPN'). Results are shown in Table 2-1. BPN' variants showing a Pi value greater than or equal to 0.5 for one or more BMI stain removal performance tests and/or TCA precipitation showed improved cleaning benefits and/or expression. Performance indices less than or equal to 0.05 were fixed to 0.05 and indicated in bold italics in the table. For every variant with a TCA protein performance index less than or equal to 0.05, all values were fixed at 0.05.

TABLE 2-1

$P_i$ Values of BPN' Variants Tested for Expression (TCA) and Stain Removal Performance (BMI pH 8/16° C., BMI pH 7/16° C., and BMI pH 8/32° C.)

| Variant Code | TCA | BMI pH 8/16° C. | BMI pH 7/16° C. | BMI pH 8/32° C. |
|---|---|---|---|---|
| Parent BPN' | 1.00 | 1.00 | 1.00 | 1.00 |
| FNA (BPN'Y217L) | 1.01 | 1.12 | 1.08 | 1.08 |
| G97A-G128A-Y217Q | 1.33 | 1.4 | 1.24 | 1.23 |
| G97A-L126A-G128A | 0.56 | 0.83 | 0.85 | 0.89 |
| G97A-L126A-G128A-Y217Q | 0.45 | 0.57 | 0.79 | 0.79 |
| G97A-L126A-Y217Q | 1.11 | 1.32 | 1.24 | 1.23 |
| G97A-M124V-G128A | 0.63 | 1.16 | 1.1 | 1.07 |
| G97A-M124V-G128A-Y217Q | 0.52 | 1.12 | 1.04 | 1.06 |
| G97A-M124V-L126A | 1.63 | 1.29 | 1.21 | 1.18 |
| G97A-M124V-L126A-G128A | 0.66 | 1.04 | 1.15 | 0.95 |
| G97A-M124V-L126A-Y217Q | 1.79 | 1.35 | 1.22 | 1.16 |
| G97A-M124V-Y217Q | 0.72 | *0.05* | *0.05* | *0.05* |
| G97A-N123G-G128A | 0.5 | 0.54 | 0.55 | 0.55 |
| G97A-N123G-G128A-Y217Q | 0.36 | 0.5 | 0.59 | 0.53 |
| G97A-N123G-L126A | 0.64 | 0.46 | 0.4 | 0.65 |
| G97A-N123G-L126A-G128A | 0.47 | *0.05* | 0.12 | *0.05* |
| G97A-N123G-L126A-Y217Q | 0.62 | 0.24 | 0.38 | 0.43 |
| G97A-N123G-M124V | 0.38 | 0.38 | 0.34 | 0.53 |
| G97A-N123G-M124V-G128A | 0.36 | *0.05* | *0.05* | *0.05* |
| G97A-N123G-M124V-L126A | 0.58 | 0.4 | 0.4 | 0.49 |
| G97A-N123G-M124V-Y217Q | *0.05* | *0.05* | *0.05* | *0.05* |
| G97A-N123G-Y217Q | 0.55 | 1.35 | 1.24 | 1.13 |
| L126A-G128A-Y217Q | 0.56 | 0.8 | 0.84 | 0.79 |
| L96T-G128A-Y217Q | 0.3 | 0.28 | 0.32 | 0.58 |
| L96T-G97A-G128A | 0.39 | 0.41 | 0.3 | 0.54 |
| L96T-G97A-G128A-Y217Q | 0.5 | 0.21 | 0.34 | 0.5 |
| L96T-G97A-L126A | 0.47 | 0.16 | 0.1 | 0.32 |

TABLE 2-1-continued

P_i Values of BPN' Variants Tested for Expression (TCA) and Stain Removal Performance (BMI pH 8/16° C., BMI pH 7/16° C., and BMI pH 8/32° C.)

| Variant Code | TCA | BMI pH 8/16° C. | BMI pH 7/16° C. | BMI pH 8/32° C. |
|---|---|---|---|---|
| L96T-G97A-L126A-G128A | 0.43 | 0.1 | 0.19 | 0.09 |
| L96T-G97A-L126A-Y217Q | 0.59 | *0.05* | 0.11 | *0.05* |
| L96T-G97A-M124V | 0.49 | 1.17 | 1.03 | 1.02 |
| L96T-G97A-M124V-G128A | 0.54 | 0.19 | 0.31 | 0.32 |
| L96T-G97A-M124V-L126A | 0.88 | 0.34 | 0.52 | 0.57 |
| L96T-G97A-M124V-Y217Q | 0.43 | 1.08 | 1.06 | 0.95 |
| L96T-G97A-N123G | 0.35 | 0.13 | 0.09 | 0.21 |
| L96T-G97A-N123G-G128A | 0.44 | *0.05* | 0.06 | *0.05* |
| L96T-G97A-N123G-L126A | 0.48 | *0.05* | *0.05* | *0.05* |
| L96T-G97A-N123G-M124V | 0.49 | 0.22 | 0.28 | 0.24 |
| L96T-G97A-N123G-Y217Q | 0.49 | *0.05* | 0.22 | 0.07 |
| L96T-G97A-Y217Q | 0.46 | 1.3 | 1.11 | 1.08 |
| L96T-L126A-G128A | 0.56 | *0.05* | *0.05* | *0.05* |
| L96T-L126A-G128A-Y217Q | 0.42 | *0.05* | 0.06 | *0.05* |
| L96T-L126A-Y217Q | 0.51 | 0.11 | 0.06 | 0.36 |
| L96T-M124V-G128A | 0.49 | 0.59 | 0.53 | 0.67 |
| L96T-M124V-G128A-Y217Q | 0.42 | 0.34 | 0.54 | 0.51 |
| L96T-M124V-L126A | 0.68 | 0.62 | 0.6 | 0.79 |
| L96T-M124V-L126A-G128A | 0.48 | *0.05* | 0.08 | 0.09 |
| L96T-M124V-L126A-Y217Q | 0.73 | 0.43 | 0.53 | 0.67 |
| L96T-M124V-Y217Q | 0.51 | 1.23 | 1.06 | 1.03 |
| L96T-N123G-G128A | 0.48 | *0.05* | *0.05* | *0.05* |
| L96T-N123G-G128A-Y217Q | 0.49 | *0.05* | 0.09 | 0.08 |
| L96T-N123G-L126A | 0.43 | *0.05* | *0.05* | *0.05* |
| L96T-N123G-L126A-G128A | 0.48 | *0.05* | *0.05* | *0.05* |
| L96T-N123G-L126A-Y217Q | 0.35 | *0.05* | *0.05* | *0.05* |
| L96T-N123G-M124V | 0.51 | *0.05* | *0.05* | 0.07 |
| L96T-N123G-M124V-G128A | 0.41 | *0.05* | 0.06 | *0.05* |
| L96T-N123G-M124V-L126A | 0.42 | 0.06 | 0.14 | *0.05* |
| L96T-N123G-M124V-Y217Q | 0.48 | 0.06 | 0.12 | 0.14 |
| L96T-N123G-Y217Q | 0.45 | 0.15 | *0.05* | 0.27 |
| M124V-G128A-Y217Q | 0.77 | 1.27 | 1.18 | 1.03 |
| M124V-L126A-G128A | 0.72 | 1.12 | 1.1 | 1.02 |
| M124V-L126A-G128A-Y217Q | 0.52 | 1.21 | 1.22 | 1.12 |
| M124V-L126A-Y217Q | 1.71 | 1.39 | 1.16 | 1.17 |
| N123G-G128A-Y217Q | 0.13 | 1 | 1.25 | 1.08 |
| N123G-L126A-G128A | 0.49 | 0.13 | 0.17 | 0.33 |
| N123G-L126A-G128A-Y217Q | 0.39 | 0.13 | 0.11 | 0.21 |
| N123G-L126A-Y217Q | 0.91 | 0.37 | 0.43 | 0.55 |
| N123G-M124V-G128A | 0.6 | *0.05* | 0.13 | 0.38 |
| N123G-M124V-G128A-Y217Q | 0.63 | *0.05* | *0.05* | *0.05* |
| N123G-M124V-L126A | 0.81 | 0.48 | 0.44 | 0.62 |
| N123G-M124V-L126A-G128A | 0.46 | 0.24 | 0.47 | 0.44 |
| N123G-M124V-L126A-Y217Q | 0.71 | 0.35 | 0.44 | 0.48 |
| N123G-M124V-Y217Q | 0.6 | 0.35 | 0.42 | 0.51 |
| N62Q-G128A-Y217Q | 0.69 | 1.3 | 1.2 | 1.13 |
| N62Q-G97A-G128A | 0.69 | 1.15 | 1.14 | 1.07 |
| N62Q-G97A-G128A-Y217Q | 0.67 | 1.15 | 1.17 | 0.98 |
| N62Q-G97A-L126A | 0.94 | 0.74 | 0.74 | 0.96 |
| N62Q-G97A-L126A-G128A | 0.47 | *0.05* | 0.23 | 0.28 |
| N62Q-G97A-L126A-Y217Q | 0.87 | 0.58 | 0.77 | 0.72 |
| N62Q-G97A-M124V | 1.17 | 1.19 | 1.08 | 1.11 |
| N62Q-G97A-M124V-G128A | 0.57 | 0.52 | 0.62 | 0.64 |
| N62Q-G97A-M124V-L126A | 1.21 | 1.03 | 1.08 | 1.03 |
| N62Q-G97A-M124V-Y217Q | 0.94 | 1.21 | 1.14 | 1.04 |
| N62Q-G97A-N123G | 0.37 | 0.58 | 0.56 | 0.58 |
| N62Q-G97A-N123G-G128A | 0.44 | *0.05* | 0.08 | 0.09 |
| N62Q-G97A-N123G-L126A | 0.53 | *0.05* | 0.07 | 0.06 |
| N62Q-G97A-N123G-M124V | 0.37 | *0.05* | 0.07 | *0.05* |
| N62Q-G97A-N123G-Y217Q | 0.51 | 0.72 | 0.8 | 0.72 |
| N62Q-G97A-Y217Q | 1.72 | 1.38 | 1.18 | 1.32 |
| N62Q-L126A-G128A | 0.48 | 0.12 | 0.13 | 0.36 |
| N62Q-L126A-G128A-Y217Q | 0.47 | 0.08 | 0.27 | 0.15 |
| N62Q-L126A-Y217Q | 0.99 | 0.93 | 0.95 | 1 |
| N62Q-L96T-G128A | 0.48 | 0.2 | 0.1 | 0.31 |
| N62Q-L96T-G128A-Y217Q | 0.9 | 0.11 | 0.26 | 0.27 |
| N62Q-L96T-G97A | 0.48 | 0.88 | 0.82 | 0.9 |
| N62Q-L96T-G97A-G128A | 0.53 | 0.15 | 0.2 | 0.25 |
| N62Q-L96T-G97A-L126A | 0.58 | *0.05* | 0.16 | 0.14 |
| N62Q-L96T-G97A-M124V | 0.64 | 0.68 | 0.74 | 0.72 |
| N62Q-L96T-G97A-N123G | 0.37 | 0.09 | 0.25 | 0.14 |
| N62Q-L96T-G97A-Y217Q | 0.57 | 0.85 | 0.74 | 0.83 |
| N62Q-L96T-L126A | 0.5 | *0.05* | *0.05* | *0.05* |
| N62Q-L96T-L126A-G128A | 0.51 | 0.09 | 0.2 | 0.18 |

TABLE 2-1-continued

P$_i$ Values of BPN' Variants Tested for Expression (TCA) and Stain Removal Performance
(BMI pH 8/16° C., BMI pH 7/16° C., and BMI pH 8/32° C.)

| Variant Code | TCA | BMI pH 8/16° C. | BMI pH 7/16° C. | BMI pH 8/32° C. |
|---|---|---|---|---|
| N62Q-L96T-L126A-Y217Q | 0.43 | 0.05 | 0.19 | 0.23 |
| N62Q-L96T-M124V | 0.44 | 0.78 | 0.72 | 0.79 |
| N62Q-L96T-M124V-G128A | 0.74 | 0.05 | 0.14 | 0.11 |
| N62Q-L96T-M124V-L126A | 0.7 | 0.25 | 0.3 | 0.44 |
| N62Q-L96T-M124V-Y217Q | 0.55 | 0.73 | 0.78 | 0.76 |
| N62Q-L96T-N123G | 0.36 | *0.05* | *0.05* | 0.06 |
| N62Q-L96T-N123G-G128A | 0.44 | *0.05* | *0.05* | *0.05* |
| N62Q-L96T-N123G-L126A | 0.42 | *0.05* | 0.14 | 0.18 |
| N62Q-L96T-N123G-M124V | 0.41 | *0.05* | *0.05* | *0.05* |
| N62Q-L96T-N123G-Y217Q | 0.5 | *0.05* | 0.08 | *0.05* |
| N62Q-L96T-Y217Q | 0.58 | 0.86 | 0.64 | 0.85 |
| N62Q-M124V-G128A | 0.46 | 0.75 | 0.71 | 0.71 |
| N62Q-M124V-G128A-Y217Q | 0.45 | 0.43 | 0.59 | 0.46 |
| N62Q-M124V-L126A | 1.62 | 1.2 | 1.06 | 1.09 |
| N62Q-M124V-L126A-G128A | 0.51 | 0.23 | 0.45 | 0.42 |
| N62Q-M124V-L126A-Y217Q | 0.97 | *0.05* | 0.09 | *0.05* |
| N62Q-M124V-Y217Q | 1.04 | 1.22 | 1.09 | 0.89 |
| N62Q-N123G-G128A | 0.41 | *0.05* | *0.05* | 0.06 |
| N62Q-N123G-G128A-Y217Q | 0.43 | *0.05* | 0.13 | 0.09 |
| N62Q-N123G-L126A | 0.55 | *0.05* | *0.05* | 0.14 |
| N62Q-N123G-L126A-G128A | 0.5 | *0.05* | *0.05* | *0.05* |
| N62Q-N123G-L126A-Y217Q | 0.54 | *0.05* | 0.09 | *0.05* |
| N62Q-N123G-M124V | 0.48 | *0.05* | *0.05* | *0.05* |
| N62Q-N123G-M124V-G128A | 0.45 | *0.05* | *0.05* | *0.05* |
| N62Q-N123G-M124V-L126A | 0.34 | *0.05* | 0.11 | 0.07 |
| N62Q-N123G-M124V-Y217Q | 0.41 | *0.05* | 0.08 | 0.1 |
| N62Q-N123G-Y217Q | 0.49 | 0.97 | 0.8 | 0.92 |

Example 3

Saturation Libraries at 97-128-217 and Additional Mutations

Saturation libraries at positions 97-128-217 in BPN' (parent) were produced by DNA 2.0. Protein concentration of culture supernatants was determined by TCA precipitation as described in Example 1. The stain removal performance of the variants was tested in laundry applications on EMPA 116 swatches (BMI stain, CFT) at pH8/16° C. using methods described in Example 1, as described in Example 2. Enzyme activity was tested by AAPF assay as described in Example 1. Functionality of BPN' variants was quantified as a performance index (Pi) (i.e., the ratio of performance of a variant relative to FNA). Results are shown in Table 3-1. BPN' variants showing a Pi value greater than or equal to 0.5 for BMI stain removal performance test and/or TCA precipitation showed improved cleaning benefits and/or expression.

TABLE 3-1

P$_i$ Values of BPN' Variants Tested for Protein Determination (TCA) and Stain Removal Performance (BMI pH 8/16° C.)

| Variant Number | Variants | TCA | BMI pH 8 16° C. |
|---|---|---|---|
| 1 | G97N-G128A-Y217M | 1.09 | 1.43 |
| 2 | G97G-G128S-Y217E | 1.53 | 1.39 |
| 3 | G97A-G128A-Y217Q | 1.34 | 1.36 |
| 4 | G97M-G128S-Y217E | 1.20 | 1.35 |
| 5 | G97A-G128S-Y217Q | 1.90 | 1.33 |
| 6 | G97D-G128S-Y217Q | 1.55 | 1.33 |
| 7 | G97M-G128G-Y217M | 1.61 | 1.33 |
| 8 | G97G-G128S-Y217Q | 1.64 | 1.32 |
| 9 | G97S-G128S-Y217Q | 1.52 | 1.32 |
| 10 | G97G-G128A-Y217Q | 1.33 | 1.30 |
| 11 | G97S-G128S-Y217E | 1.03 | 1.30 |
| 12 | G97A-G128S-Y217L | 2.18 | 1.29 |
| 13 | G97A-G128A-Y217N | 1.22 | 1.28 |
| 14 | G97Q-G128S-Y217L | 1.89 | 1.28 |
| 15 | G97A-G128A-Y217M | 1.45 | 1.28 |
| 16 | G97A-G128A-Y217S | 1.35 | 1.27 |
| 17 | G97D-G128A-Y217Q | 1.14 | 1.27 |
| 18 | G97M-G128S-Y217Q | 0.99 | 1.27 |
| 19 | G97Q-G128G-Y217D-S87Y | 1.45 | 1.27 |
| 20 | G97S-G128A-Y217N | 1.09 | 1.27 |
| 21 | G97A-G128S-Y217T | 1.61 | 1.27 |
| 22 | G97D-G128S-Y217E | 1.01 | 1.27 |
| 23 | G97D-G128A-Y217L | 1.38 | 1.26 |
| 24 | G97G-G128S-Y217E-S78P-A272T | 1.00 | 1.26 |
| 25 | G97T-G128S-Y217D | 1.13 | 1.26 |
| 26 | G97D-G128A-Y217I | 0.99 | 1.26 |
| 27 | G97Q-G128S-Y217Q | 1.59 | 1.26 |
| 28 | G97G-G128A-Y217D | 1.12 | 1.25 |
| 29 | G97Q-G128A-Y217N | 1.09 | 1.25 |
| 30 | G97S-G128A-Y217M | 1.41 | 1.25 |
| 31 | G97S-G128S-Y217N | 1.55 | 1.25 |
| 32 | G97S-G128S-Y217M | 1.53 | 1.25 |
| 33 | G97E-G128S-Y217M | 1.58 | 1.24 |
| 34 | G97S-G128P-Y217Q | 0.99 | 1.24 |
| 35 | G97T-G128S-Y217Q | 1.06 | 1.24 |
| 36 | G97D-G128S-Y217Q-A73T | 1.18 | 1.23 |
| 37 | G97E-G128S-Y217N | 1.24 | 1.23 |
| 38 | G97G-G128A-Y217I | 1.51 | 1.23 |
| 39 | G97Q-G128A-Y217D | 1.14 | 1.23 |
| 40 | G97Q-G128S-Y217M | 1.98 | 1.23 |
| 41 | G97R-G128T-Y217Q-S162P | 0.68 | 1.23 |
| 42 | G97S-G128S-Y217D | 1.50 | 1.23 |
| 43 | G97T-G128P-Y217I | 1.30 | 1.23 |

TABLE 3-1-continued

P_i Values of BPN' Variants Tested for Protein Determination (TCA) and Stain Removal Performance (BMI pH 8/16° C.)

| Variant Number | Variants | TCA | BMI pH 8 16° C. |
|---|---|---|---|
| 44 | G97Q-G128G-Y217E | 1.58 | 1.23 |
| 45 | G97C-G128G-Y217N | 1.26 | 1.22 |
| 46 | G97D-G128S-Y217H | 1.49 | 1.22 |
| 47 | G97M-G128S-Y217L | 1.02 | 1.22 |
| 48 | G97M-G128S-Y217N | 0.98 | 1.21 |
| 49 | G97S-G128S-Y217E | 0.59 | 1.21 |
| 50 | G97M-G128S-Y217I | 1.11 | 1.19 |
| 51 | G97A-G128P-Y217A | 0.84 | 1.18 |
| 52 | G97R-G128S-Y217D | 0.95 | 1.16 |
| 53 | G97D-G128A-Y217D | 0.75 | 1.15 |
| 54 | G97V-G128G-Y217D | 0.71 | 1.14 |
| 55 | G97V-G128G-Y217E | 0.72 | 1.13 |
| 56 | G97A-G128G-Y217T | 1.29 | 1.12 |
| 57 | G97G-G128N-Y217L | 0.82 | 1.12 |
| 58 | G97D-G128A-Y217T | 0.69 | 1.11 |
| 59 | G97M-G128A-Y217E | 0.64 | 1.11 |
| 60 | G97M-G128A-Y217N | 0.58 | 1.06 |
| FNA | G97G-G128G-Y217L | 1.00 | 1.00 |

Example 4

Additional Library Designs and Stain Removal Performance of Variants

Additional BPN' multiple mutation libraries were produced by Geneart or Gene Oracle, using BPN': G97A-G128A-Y217Q protein as the parent molecule. Results of experiments conducted to determine stain removal activity (microswatch assay to determine stain removal performance in laundry applications using EMPA 116 swatches (BMI stain, CFT Vlaardingen) (BMI pH8, BMI pH7, BMI 32° C.), protein determination by TCA precipitation, and LAS/EDTA stability (tests of properties of interest) of BPN' variants are shown in Tables 4-1, 4-2, 4-3, and 4-4.

The results were obtained using the methods described in Example 1, with the following modifications for the stain removal performance assay. The test detergent used was heat inactivated TIDE® 2x Cold detergent (Procter & Gamble, Cincinnati, Ohio, USA).

Heat inactivation of commercial detergent formulas serves to destroy the endogenous enzymatic activity of any protein components while retaining the properties of non-enzymatic components. Heat inactivation of the detergents was performed by placing pre-weighed amounts of liquid detergent (in a glass bottle) in a water bath at 95° C. for 2 hours. The detergent was purchased from local supermarket stores. Both unheated and heated detergents were assayed within 5 minutes of dissolving the detergent to accurately determine enzyme percentage deactivated. Enzyme activity was tested by AAPF assay. As described throughout herein, functionality of BPN' variants was quantified as a performance index (Pi), which is the ratio of performance of a variant to parent protein BPN': G97A-G128A-Y217Q. BPN': G97A-G128A-Y217Q variants showing a Pi value greater or equal than 0.5 for BMI stain removal performance and/or TCA precipitation showed improved cleaning benefits and/or expression. Performance indices less than or equal to 0.05 were fixed to 0.05 and indicated in bold italics in the table.

TABLE 4-1

Stain removal performance of multiple mutation variants of BPN': G97A-G128A-Y217Q Parent

| Variant | BMI pH 8 | BMI pH 7 | BMI 32° C. | TCA |
|---|---|---|---|---|
| S145D | 1.06 | 1.03 | 1.18 | 0.96 |
| P239R | 1.03 | 0.98 | 1.11 | 0.67 |
| N61E P129E S162K K213L N240K | 1.02 | 0.93 | 1.05 | 0.98 |
| N61E | 1.02 | 0.98 | 1.09 | 1.33 |
| P40E A144K K213L | 1.01 | 0.92 | 0.91 | 0.80 |
| P129E | 0.99 | 1.01 | 1.03 | 1.04 |
| N61E P129E S159K | 0.99 | 0.98 | 1.07 | 1.19 |
| K213L | 0.98 | 1.00 | 1.03 | 1.06 |
| S87D | 0.98 | 1.03 | 1.02 | 0.75 |
| Q206E | 0.97 | 0.96 | 0.98 | 1.01 |
| S24R P40E S145D S159K K213L | 0.97 | 0.96 | 0.98 | 0.91 |
| K265N | 0.96 | 1.00 | 1.00 | 0.93 |
| S24R | 0.96 | 0.87 | 0.99 | 0.99 |
| P40E | 0.96 | 0.96 | 0.96 | 0.80 |
| Q275E | 0.95 | 1.01 | 0.95 | 0.99 |
| P129E S145D N240K | 0.95 | 0.97 | 0.98 | 0.82 |
| A144K | 0.95 | 0.87 | 0.95 | 0.93 |
| S159K | 0.94 | 0.90 | 0.96 | 1.03 |
| S162K | 0.94 | 0.92 | 1.01 | 0.96 |
| N240K | 0.94 | 0.92 | 1.03 | 0.71 |
| S24R S87D Q206E | 0.90 | 0.95 | 0.98 | 0.83 |
| S87D S162K K265N | 0.89 | 0.96 | 0.93 | 0.64 |
| N61E S145D S162K K213L T242R | 0.88 | 0.95 | 0.89 | 0.72 |
| S87D A144K S145D S159K Q275E | 0.88 | 0.91 | 0.96 | 0.72 |
| S24R S87D A144K K265N Q275E | 0.88 | 0.94 | 0.93 | 0.55 |
| T242R | 0.87 | 0.84 | 0.83 | 0.53 |
| P40E N61E P129E A144K S162K K213L N240K | 0.85 | 0.88 | 0.89 | 0.64 |
| S24R P40E N61E A144K Q206E K213L T242R | 0.85 | 0.81 | 0.91 | 0.45 |
| P129E P239R K265N | 0.83 | 0.93 | 0.86 | 0.59 |
| S24R P129E Q206E N240K K265N | 0.81 | 0.86 | 0.82 | 0.63 |
| P40E S145D S159K S162K K213L P239R Q275E | 0.78 | 0.82 | 0.83 | 0.47 |
| Q103E | 0.67 | 0.84 | 0.72 | 0.46 |
| S87D T242R Q275E | 0.60 | 0.74 | 0.62 | 0.38 |

TABLE 4-1-continued

Stain removal performance of multiple mutation variants of BPN':
G97A-G128A-Y217Q Parent

| Variant | BMI pH 8 | BMI pH 7 | BMI 32° C. | TCA |
|---|---|---|---|---|
| P129E S145D N240K T242R K265N | 0.58 | 0.72 | 0.68 | 0.37 |
| N62R | 0.58 | 0.63 | 0.64 | 0.44 |
| P40E N61E S87D K162K T242R | 0.55 | 0.62 | 0.58 | 0.29 |
| P40E N61E S87D P129E S159K S162K T242R | 0.52 | 0.47 | 0.57 | 0.27 |
| P40E N61E Q103E A144K S159K S162K Q275E | 0.44 | 0.50 | 0.53 | 0.30 |
| N61E Q103E N240K | 0.44 | 0.62 | 0.51 | 0.42 |
| S87D T242R K265N | 0.42 | 0.60 | 0.48 | 0.28 |
| Q103E S162K Q206E K213L P239R | 0.42 | 0.53 | 0.46 | 0.31 |
| P40E N61E Q103E S159K S162K K213L P239R | 0.39 | 0.43 | 0.50 | 0.25 |
| P40E N61E Q103E S159K S162K K213L N240K | 0.38 | 0.40 | 0.49 | 0.26 |
| N61E Q103E A144K K213L T242R | 0.36 | 0.38 | 0.49 | 0.27 |
| N62R K265N Q275E | 0.29 | 0.42 | 0.32 | 0.38 |
| N62R S159K Q206E K265N Q275E | 0.26 | 0.35 | 0.33 | 0.35 |
| S24R Q103E P129E N240K K265N | 0.24 | 0.29 | 0.27 | 0.24 |
| N62R S87D P129E S145D S159K S162K Q275E | 0.24 | 0.25 | 0.33 | 0.30 |
| Q103E P129E T242R | 0.23 | 0.28 | 0.31 | 0.28 |
| S24R N61E Q103E P129E K213L N240K T242R | 0.22 | 0.15 | 0.27 | 0.25 |
| P40E N62R S145D S159K S162K Q206E Q275E | 0.21 | 0.24 | 0.31 | 0.32 |
| S24R P40E N61E S87D Q103E S159K S162K K213L N240K | 0.19 | 0.21 | 0.25 | 0.23 |
| N62R S87D S145D S159K S162K K265N Q275E | 0.19 | 0.22 | 0.19 | 0.33 |
| P40E N61E N62R S87D S159K S162K K265N | 0.18 | 0.19 | 0.21 | 0.28 |
| N61E S87D Q103E S159K S162K K213L T242R | 0.17 | 0.13 | 0.17 | 0.25 |
| N61E Q103E P129E P239R N240K | 0.14 | 0.18 | 0.23 | 0.33 |
| P40E N62R S87D S145D S159K S162K Q275E | 0.14 | 0.14 | 0.27 | 0.33 |
| S24R N62R S87D S145D K265N | 0.13 | 0.22 | 0.16 | 0.32 |
| N62R S87D S145D S159K S162K K213L N240K K265N Q275E | 0.11 | 0.11 | 0.12 | 0.32 |
| S24R N61E Q103E P129E Q206E P239R N240K | 0.09 | *0.05* | *0.05* | 0.26 |
| N61E Q103E A144K Q206E K213L N240K T242R | 0.07 | *0.05* | 0.15 | 0.31 |
| S24R Q103E P129E S145D P239R N240K K265N | 0.06 | *0.05* | *0.05* | 0.26 |
| S24R N61E Q103E P129E Q206E K213L P239R N240K T242R | *0.05* | *0.05* | *0.05* | 0.43 |
| N61E Q103E P129E K213L P239R N240K T242R | *0.05* | *0.05* | *0.05* | 0.38 |
| P40E N62R S87D Q103E A144K S159K Q275E | *0.05* | *0.05* | *0.05* | 0.25 |
| N61E N62R S87D Q103E S159K S162K K213L T242R Q275E | *0.05* | *0.05* | *0.05* | 0.33 |
| S24R P40E N61E Q103E P129E A144K K213L P239R N240K T242R K265N | *0.05* | *0.05* | *0.05* | 0.36 |
| S24R Q103E P129E S145D Q206E P239R N240K T242R K265N | *0.05* | *0.05* | *0.05* | 0.38 |
| P40E N62R S87D Q103E S162K | *0.05* | *0.05* | *0.05* | 0.29 |
| N61E Q103E Q206E K213L P239R N240K T242R | *0.05* | *0.05* | *0.05* | 0.32 |
| S24R P40E N61E Q103E P129E A144K Q206E K213L P239R N240K T242R | *0.05* | *0.05* | *0.05* | 0.37 |
| S24R N61E Q103E P129E A144K S145D Q206E K213L P239R N240K T242R | *0.05* | *0.05* | *0.05* | 0.38 |
| S24R N61E Q103E P129E S145D P239R N240K T242R K265N | *0.05* | *0.05* | *0.05* | 0.35 |
| S24R P40E N61E Q103E P129E A144K S145D K213L P239R N240K T242R | *0.05* | *0.05* | *0.05* | 0.34 |
| N61E S87D Q103E P129E S159K S162K K213L N240K T242R | *0.05* | *0.05* | *0.05* | 0.25 |
| S24R P40E N61E S87D Q103E P129E A144K S162K Q206E K213L P239R N240K T242R | *0.05* | *0.05* | *0.05* | 0.35 |
| S24R N61E S87D Q103E P129E A144K Q206E K213L P239R N240K T242R | *0.05* | *0.05* | *0.05* | 0.34 |
| S24R N62R P129E S145D P239R K265N Q275E | *0.05* | *0.05* | *0.05* | 0.28 |
| P40E N61E S87D Q103E S145D S159K S162K K213L P239R N240K T242R | *0.05* | *0.05* | *0.05* | 0.30 |
| P40E N61E Q103E P129E A144K S162K Q206E K213L P239R N240K T242R | *0.05* | *0.05* | *0.05* | 0.37 |
| S24R N62R P129E Q206E N240K K265N Q275E | *0.05* | *0.05* | *0.05* | 0.28 |
| P40E N62R S87D S145D S159K S162K N240K K265N Q275E | *0.05* | *0.05* | *0.05* | 0.27 |
| P40E N62R S87D S159K S162K K265N Q275E | *0.05* | 0.06 | 0.06 | 0.30 |
| S24R P40E N61E Q103E P129E S162K Q206E K213L P239R N240K T242R | *0.05* | *0.05* | *0.05* | 0.37 |
| N61E Q103E P129E A144K Q206E K213L P239R N240K T242R | *0.05* | *0.05* | *0.05* | 0.34 |

TABLE 4-1-continued

Stain removal performance of multiple mutation variants of BPN':
G97A-G128A-Y217Q Parent

| Variant | BMI pH 8 | BMI pH 7 | BMI 32° C. | TCA |
|---|---|---|---|---|
| S24R P40E N61E S87D Q103E P129E A144K K213L P239R N240K T242R | *0.05* | *0.05* | *0.05* | 0.33 |
| P40E N61E Q103E P129E A144K K213L P239R N240K T242R | *0.05* | *0.05* | *0.05* | 0.34 |
| S24R N61E Q103E P129E A144K Q206E K213L P239R N240K T242R K265N | *0.05* | *0.05* | *0.05* | 0.43 |

The LAS/EDTA stability of the BPN' multiple mutation libraries was tested and compared to BPN': G97A-G128A-Y217Q. The LAS/EDTA assay was performed as described in LAS Stability assay in Example 1 except that the stress buffer contained 0.1% LAS+10 mM EDTA and the stress plates were incubated at 40° C. for 30 minutes. The functionality of BPN' variants was quantified as a performance index (Pi), which is the ratio of performance of a variant to parent protein BPN': G97A-G128A-Y217Q. The results are shown in Table 4-2.

TABLE 4-2

Stain removal performance of multiple mutation variants
of BPN': G97A-G128A-Y217Q Parent

| Variant | Mutations | | BMI pH8 | BMI pH7 | TCA | LAS/EDTA |
|---|---|---|---|---|---|---|
| LHS1 | S53G | | 1.05 | 1.03 | 1.18 | 0.98 |
| LHS2 | F58G | | 0.38 | 0.43 | 0.50 | 0.99 |
| LHS3 | S78N | | 0.99 | 1.00 | 1.00 | 1.50 |
| LHS4 | Y104N | | 0.36 | 0.53 | 0.73 | 1.49 |
| LHS5 | I111V | | 0.91 | 0.95 | 0.75 | 1.19 |
| LHS6 | A114G | | 0.71 | 0.72 | 0.60 | 0.93 |
| LHS7 | N117S | | 0.80 | 0.88 | 0.66 | 0.97 |
| LHS8 | S125A | | 0.73 | 0.79 | 0.85 | 0.97 |
| LHS9 | S132N | | 0.86 | 0.80 | 0.59 | 1.03 |
| LHS10 | P239V | | 0.42 | 0.43 | 0.47 | 1.22 |
| LHS11 | S53G | F58G | 0.67 | 0.71 | 0.49 | 0.75 |
| LHS12 | S53G | S78N | 0.98 | 0.99 | 1.10 | 1.44 |
| LHS13 | S53G | Y104N | 0.35 | 0.56 | 0.71 | 1.47 |
| LHS14 | S53G | I111V | 0.99 | 0.99 | 0.83 | 1.20 |
| LHS15 | S53G | A114G | 0.85 | 0.91 | 0.64 | 1.15 |
| LHS16 | S53G | N117S | 0.93 | 1.00 | 0.75 | 1.30 |
| LHS17 | S53G | S125A | 0.71 | 0.76 | 0.85 | 0.87 |
| LHS18 | S53G | S132N | 0.93 | 0.93 | 0.74 | 1.03 |
| LHS19 | S53G | P239V | 0.52 | 0.59 | 0.46 | 1.12 |
| LHS20 | F58G | S78N | 0.44 | 0.49 | 0.50 | 1.32 |
| LHS21 | F58G | Y104N | *0.05* | *0.05* | 0.56 | 1.67 |
| LHS22 | F58G | I111V | 0.15 | 0.19 | 0.52 | 1.33 |
| LHS23 | F58G | A114G | *0.05* | *0.05* | 0.59 | 1.59 |
| LHS24 | F58G | N117S | 0.09 | 0.09 | 0.53 | 1.47 |
| LHS25 | F58G | S125A | *0.05* | *0.05* | 0.56 | 1.56 |
| LHS26 | F58G | S132N | 0.07 | 0.07 | 0.49 | 1.17 |
| LHS27 | F58G | P239V | *0.05* | *0.05* | 0.52 | 1.64 |
| LHS28 | S78N | Y104N | 0.37 | 0.56 | 0.67 | 1.71 |
| LHS29 | S78N | I111V | 0.92 | 0.92 | 0.71 | 1.53 |
| LHS30 | S78N | A114G | 0.74 | 0.75 | 0.48 | 1.49 |
| LHS31 | S78N | N117S | 0.83 | 0.87 | 0.61 | 1.51 |
| LHS32 | S78N | S125A | 0.77 | 0.79 | 0.89 | 1.33 |
| LHS33 | S78N | S132N | 0.81 | 0.76 | 0.60 | 1.38 |
| LHS34 | S78N | P239V | 0.40 | 0.47 | 0.50 | 1.66 |
| LHS35 | Y104N | I111V | 0.21 | 0.31 | 0.64 | 1.55 |
| LHS36 | Y104N | A114G | *0.05* | 0.06 | 0.59 | 1.70 |
| LHS37 | Y104N | N117S | 0.08 | 0.14 | 0.45 | 1.72 |
| LHS38 | Y104N | S125A | 0.06 | 0.09 | 0.64 | 1.77 |
| LHS39 | Y104N | S132N | 0.98 | 1.07 | 0.74 | 1.26 |
| LHS40 | Y104N | P239V | *0.05* | *0.05* | 0.69 | 1.82 |
| LHS41 | I111V | A114G | 0.15 | 0.16 | 0.43 | 1.24 |
| LHS42 | I111V | N117S | 0.45 | 0.43 | 0.51 | 1.12 |
| LHS43 | I111V | S125A | 0.37 | 0.47 | 0.62 | 1.21 |
| LHS44 | I111V | S132N | 0.53 | 0.58 | 0.41 | 1.00 |
| LHS45 | I111V | P239V | 0.24 | 0.31 | 0.40 | 1.29 |
| LHS46 | A114G | N117S | 0.14 | 0.15 | 0.48 | 1.37 |
| LHS47 | A114G | S125A | 0.20 | 0.29 | 0.58 | 1.41 |
| LHS48 | A114G | S132N | 0.24 | 0.25 | 0.50 | 1.14 |
| LHS49 | A114G | P239V | *0.05* | 0.07 | 0.48 | 1.48 |
| LHS50 | N117S | S125A | 0.31 | 0.39 | 0.48 | 1.27 |
| LHS51 | N117S | S132N | 0.35 | 0.35 | 0.45 | 1.12 |

TABLE 4-2-continued

Stain removal performance of multiple mutation variants of BPN': G97A-G128A-Y217Q Parent

| Variant | Mutations | | | BMI pH8 | BMI pH7 | TCA | LAS/EDTA |
|---|---|---|---|---|---|---|---|
| LHS52 | N117S | P239V | | 0.15 | 0.19 | 0.38 | 1.32 |
| LHS53 | S125A | S132N | | 0.38 | 0.51 | 0.47 | 1.03 |
| LHS54 | S125A | P239V | | 0.09 | 0.12 | 0.47 | 1.59 |
| LHS55 | S132N | P239V | | 0.16 | 0.22 | 0.45 | 1.29 |
| LHS56 | S53G | F58G | S78N | 0.72 | 0.76 | 0.56 | 1.48 |
| LHS57 | S53G | F58G | Y104N | *0.05* | *0.05* | 0.52 | 1.78 |
| LHS58 | S53G | F58G | I111V | 0.35 | 0.43 | 0.38 | 1.16 |
| LHS59 | S53G | F58G | A114G | 0.10 | 0.14 | 0.46 | 1.37 |
| LHS60 | S53G | F58G | N117S | 0.22 | 0.30 | 0.41 | 1.19 |
| LHS61 | S53G | F58G | S125A | 0.18 | 0.23 | 0.44 | 1.46 |
| LHS62 | S53G | F58G | S132N | 0.29 | 0.32 | 0.41 | 1.01 |
| LHS63 | S53G | F58G | P239V | 0.06 | 0.08 | 0.49 | 1.54 |
| LHS64 | S53G | S78N | Y104N | 0.43 | 0.63 | 0.76 | 1.80 |
| LHS65 | S53G | S78N | I111V | 0.97 | 1.01 | 0.89 | 1.69 |
| LHS66 | S53G | S78N | A114G | 0.85 | 0.89 | 0.60 | 1.63 |
| LHS67 | S53G | S78N | N117S | 0.94 | 0.92 | 0.69 | 1.61 |
| LHS68 | S53G | S78N | S125A | 0.78 | 0.82 | 0.90 | 1.37 |
| LHS69 | S53G | S78N | S132N | 0.96 | 0.93 | 0.75 | 1.48 |
| LHS70 | S53G | S78N | P239V | 0.62 | 0.66 | 0.44 | 1.59 |
| LHS71 | S53G | Y104N | I111V | 0.25 | 0.41 | 0.63 | 1.73 |
| LHS72 | S53G | Y104N | A114G | 0.08 | 0.09 | 0.53 | 1.75 |
| LHS73 | S53G | Y104N | N117S | *0.05* | 0.12 | 0.50 | 1.68 |
| LHS74 | S53G | Y104N | S125A | 0.20 | 0.23 | 0.50 | 1.20 |
| LHS75 | S53G | Y104N | S132N | 0.94 | 1.00 | 1.21 | 1.10 |
| LHS76 | S53G | Y104N | P239V | *0.05* | *0.05* | 0.54 | 1.63 |
| LHS77 | S53G | I111V | A114G | 0.48 | 0.51 | 0.47 | 1.25 |
| LHS78 | S53G | I111V | N117S | 0.66 | 0.74 | 0.48 | 1.17 |
| LHS79 | S53G | I111V | S125A | 0.49 | 0.64 | 0.72 | 1.27 |
| LHS80 | S53G | I111V | S132N | 0.78 | 0.80 | 0.54 | 1.19 |
| LHS81 | S53G | I111V | P239V | 0.32 | 0.38 | 0.43 | 1.26 |
| LHS82 | S53G | A114G | N117S | 0.16 | 0.29 | 0.47 | 1.19 |
| LHS83 | S53G | A114G | S125A | 0.32 | 0.44 | 0.50 | 1.19 |
| LHS84 | S53G | A114G | S132N | 0.44 | 0.50 | 0.40 | 1.05 |
| LHS85 | S53G | A114G | P239V | 0.15 | 0.31 | 0.44 | 1.42 |
| LHS86 | S53G | N117S | S125A | 0.50 | 0.56 | 0.54 | 1.08 |
| LHS87 | S53G | N117S | S132N | 0.54 | 0.59 | 0.49 | 1.15 |
| LHS88 | S53G | N117S | P239V | 0.28 | 0.41 | 0.50 | 1.31 |
| LHS89 | S53G | S125A | S132N | 0.50 | 0.55 | 0.67 | N/D |
| LHS90 | S53G | S125A | P239V | 0.06 | 0.12 | 0.59 | N/D |
| LHS91 | S53G | S132N | P239V | 0.27 | 0.33 | 0.49 | N/D |
| LHS92 | F58G | S78N | Y104N | *0.05* | *0.05* | 0.67 | N/D |
| LHS93 | F58G | S78N | I111V | 0.17 | 0.18 | 0.56 | N/D |
| LHS94 | F58G | S78N | A114G | *0.05* | 0.07 | 0.67 | N/D |
| LHS95 | F58G | S78N | N117S | 0.11 | 0.12 | 0.64 | N/D |
| LHS96 | F58G | S78N | S125A | 0.11 | 0.15 | 0.65 | N/D |
| LHS97 | F58G | S78N | S132N | 0.06 | 0.12 | 0.57 | N/D |
| LHS98 | F58G | S78N | P239V | *0.05* | *0.05* | 0.60 | N/D |
| LHS99 | F58G | Y104N | I111V | *0.05* | *0.05* | 0.57 | N/D |
| LHS100 | F58G | Y104N | A114G | *0.05* | *0.05* | 0.59 | N/D |
| LHS101 | F58G | Y104N | N117S | *0.05* | *0.05* | 0.61 | N/D |
| LHS102 | F58G | Y104N | S125A | *0.05* | *0.05* | 0.61 | N/D |
| LHS103 | F58G | Y104N | S132N | 0.19 | 0.28 | 0.48 | N/D |
| LHS104 | F58G | Y104N | P239V | *0.05* | *0.05* | 0.62 | N/D |
| LHS105 | F58G | I111V | A114G | *0.05* | *0.05* | 0.62 | N/D |
| LHS106 | F58G | I111V | N117S | *0.05* | *0.05* | 0.58 | N/D |
| LHS107 | F58G | I111V | S125A | *0.05* | *0.05* | 0.53 | N/D |
| LHS108 | F58G | I111V | S132N | *0.05* | *0.05* | 0.52 | N/D |
| LHS109 | F58G | I111V | P239V | *0.05* | *0.05* | 0.55 | N/D |
| LHS110 | F58G | A114G | N117S | *0.05* | *0.05* | 0.64 | N/D |
| LHS111 | F58G | A114G | S125A | *0.05* | *0.05* | 0.62 | N/D |
| LHS112 | F58G | A114G | S132N | *0.05* | *0.05* | 0.58 | N/D |
| LHS113 | F58G | A114G | P239V | *0.05* | *0.05* | 0.45 | N/D |
| LHS114 | F58G | N117S | S125A | *0.05* | *0.05* | 0.60 | N/D |
| LHS115 | F58G | N117S | S132N | *0.05* | *0.05* | 0.55 | N/D |
| LHS116 | F58G | N117S | P239V | *0.05* | *0.05* | 0.52 | N/D |
| LHS117 | F58G | S125A | S132N | *0.05* | *0.05* | 0.62 | N/D |
| LHS118 | F58G | S125A | P239V | *0.05* | *0.05* | 0.62 | N/D |
| LHS119 | F58G | S132N | P239V | *0.05* | *0.05* | 0.65 | N/D |
| LHS120 | S78N | I111V | | 0.33 | 0.44 | 0.63 | N/D |
| LHS121 | S78N | Y104N | A114G | *0.05* | *0.05* | 0.68 | N/D |
| LHS122 | S78N | Y104N | N117S | *0.05* | 0.13 | 0.60 | N/D |
| LHS123 | S78N | Y104N | S125A | *0.05* | 0.06 | 0.69 | N/D |
| LHS124 | S78N | Y104N | S132N | 1.02 | 1.00 | 0.77 | N/D |
| LHS125 | S78N | Y104N | P239V | *0.05* | *0.05* | 0.65 | N/D |

TABLE 4-2-continued

Stain removal performance of multiple mutation variants of BPN': G97A-G128A-Y217Q Parent

| Variant | Mutations | | | BMI pH8 | BMI pH7 | TCA | LAS/EDTA |
|---|---|---|---|---|---|---|---|
| LHS126 | S78N | I111V | A114G | 0.35 | 0.36 | 0.60 | N/D |
| LHS127 | S78N | I111V | N117S | 0.52 | 0.53 | 0.54 | N/D |
| LHS128 | S78N | I111V | S125A | 0.51 | 0.57 | 0.67 | N/D |
| LHS129 | S78N | I111V | S132N | 0.50 | 0.46 | 0.49 | N/D |
| LHS130 | S78N | I111V | P239V | 0.27 | 0.29 | 0.55 | N/D |
| LHS131 | S78N | A114G | N117S | 0.11 | 0.14 | 0.50 | N/D |
| LHS132 | S78N | A114G | S125A | 0.27 | 0.27 | 0.51 | N/D |
| LHS133 | S78N | A114G | S132N | 0.23 | 0.21 | 0.56 | N/D |
| LHS134 | S78N | A114G | P239V | 0.12 | 0.11 | 0.54 | N/D |
| LHS135 | S78N | N117S | S125A | 0.39 | 0.48 | 0.62 | N/D |
| LHS136 | S78N | N117S | S132N | 0.42 | 0.47 | 0.55 | N/D |
| LHS137 | S78N | N117S | P239V | 0.09 | *0.05* | 0.53 | N/D |
| LHS138 | S78N | S125A | S132N | 0.46 | 0.47 | 0.56 | N/D |
| LHS139 | S78N | S125A | P239V | 0.06 | 0.08 | 0.64 | N/D |
| LHS140 | S78N | S132N | P239V | 0.21 | 0.16 | 0.45 | N/D |
| LHS141 | Y104N | I111V | A114G | *0.05* | 0.06 | 0.63 | N/D |
| LHS142 | Y104N | I111V | N117S | 0.05 | 0.05 | 0.57 | N/D |
| LHS143 | Y104N | I111V | S125A | 0.05 | 0.09 | 0.66 | N/D |
| LHS144 | Y104N | I111V | S132N | 0.87 | 0.91 | 0.60 | N/D |
| LHS145 | Y104N | I111V | P239V | *0.05* | *0.05* | 0.61 | N/D |
| LHS146 | Y104N | A114G | N117S | *0.05* | *0.05* | 0.53 | N/D |
| LHS147 | Y104N | A114G | S125A | *0.05* | *0.05* | 0.50 | N/D |
| LHS148 | Y104N | A114G | S132N | 0.32 | 0.45 | 0.50 | N/D |
| LHS149 | Y104N | A114G | P239V | 0.05 | 0.05 | 0.62 | N/D |
| LHS150 | Y104N | N117S | S125A | 0.05 | *0.05* | 0.56 | N/D |
| LHS151 | Y104N | N117S | S132N | 0.53 | 0.63 | 0.54 | N/D |
| LHS152 | Y104N | N117S | P239V | 0.06 | *0.05* | 0.66 | N/D |
| LHS153 | Y104N | S125A | S132N | 0.30 | 0.41 | 0.69 | N/D |
| LHS154 | Y104N | S125A | P239V | *0.05* | *0.05* | 0.54 | N/D |
| LHS155 | Y104N | S132N | P239V | 0.25 | 0.36 | 0.50 | N/D |
| LHS156 | I111V | A114G | N117S | *0.05* | 0.05 | 0.54 | N/D |
| LHS157 | I111V | A114G | S125A | 0.05 | 0.06 | 0.59 | N/D |
| LHS158 | I111V | A114G | S132N | *0.05* | *0.05* | 0.58 | N/D |
| LHS159 | I111V | A114G | P239V | *0.05* | *0.05* | 0.63 | N/D |
| LHS160 | I111V | N117S | S125A | 0.10 | 0.10 | 0.66 | N/D |
| LHS161 | I111V | N117S | S132N | *0.05* | *0.05* | 0.55 | N/D |
| LHS162 | I111V | N117S | P239V | *0.05* | *0.05* | 0.55 | N/D |
| LHS163 | I111V | S125A | S132N | *0.05* | 0.14 | 0.56 | N/D |
| LHS164 | I111V | S125A | P239V | *0.05* | *0.05* | 0.60 | N/D |
| LHS165 | I111V | S132N | P239V | *0.05* | *0.05* | 0.57 | N/D |
| LHS166 | A114G | N117S | S125A | *0.05* | *0.05* | 0.57 | N/D |
| LHS167 | A114G | N117S | S132N | *0.05* | 0.07 | 0.52 | N/D |
| LHS168 | A114G | N117S | P239V | *0.05* | *0.05* | 0.67 | N/D |
| LHS169 | A114G | S125A | S132N | *0.05* | *0.05* | 0.59 | N/D |
| LHS170 | A114G | S125A | P239V | *0.05* | *0.05* | 0.63 | N/D |
| LHS171 | A114G | S132N | P239V | *0.05* | *0.05* | 0.55 | N/D |
| LHS172 | N117S | S125A | S132N | *0.05* | 0.05 | 0.56 | N/D |
| LHS173 | N117S | S125A | P239V | *0.05* | *0.05* | 0.56 | N/D |
| LHS174 | N117S | S132N | P239V | *0.05* | *0.05* | 0.57 | N/D |
| LHS175 | S125A | S132N | P239V | *0.05* | *0.05* | 0.55 | N/D |
| LHS176 | N76D | D120H | K213N M222Q | 0.22 | 0.31 | 0.68 | N/D |

The LAS/EDTA stability of the BPN' triple variants was tested and compared to BPN'-Y217L. The LAS/EDTA assay was performed as described in the "LAS Stability Assay" section of Example 1, except that the stress buffer contained 0.1% LAS+10 mM EDTA and the stress plates were incubated at 35° C. for 25 minutes. The functionality of BPN' variants was quantified as a performance index (Pi), which is the ratio of performance of a variant to parent protein BPN'-Y217L. Results are shown in Table 4-3.

TABLE 4-3

LAS/EDTA Stability Results for BPN' Variants

| Variant | Pi LAS/EDTA |
|---|---|
| N62Q-G97A-Y217Q | 1.26 |
| G97A-N123G-Y217Q | 0.95 |
| G97A-G128A-Y217Q | 1.24 |
| FNA: G97G-G128G-Y217L | 1.00 |

All patents and publications mentioned in the specification are indicative of the levels of those skilled in the art to which the invention pertains. Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by herein.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not excised material is specifically recited herein.

What is claimed is:

1. A fabric or dishware cleaning composition comprising at least one subtilisin variant, wherein the subtilisin variant has at least 95% sequence identity to the mature subtilisin protease having the amino acid sequence of SEQ ID NO:1, the subtilisin variant comprises, compared to the mature subtilisin protease having the amino acid sequence of SEQ ID NO:1, the substitutions G97A-G128A-Y217Q wherein said substitutions are at positions equivalent to the positions of BPN' subtilisin set forth in SEQ ID NO:1 and wherein the subtilisin variant has improved activity compared with SEQ ID NO: 1;

wherein the variant has at least one of multiple mutation variants selected from the group consisting of S24R, N61E, Q103E, P129E, A144K, Q206E, K213L, P239R, N240K, T242R, K265N; P40E, N61E, Q103E, P129E, A144K, K213L, P239R, N240K, T242R; S24R, P40E, N61E, S87D, Q103E, P129E, A144K, K213L, P239R, N240K, T242R; N61E, Q103E, P129E, A144K, Q206E, K213L, P239R, N240K, T242R; S24R, P40E, N61E, Q103E, P129E, S162K, Q206E, K213L, P239R, N240K, T242R; P40E, N62R, S87D, S145D, S159K, S162K, N240K, K265N, Q275E; S24R, N62R, P129E, Q206E, N240K, K265N, Q275E; P40E, N61E, Q103E, P129E, A144K, S162K, Q206E, K213L, P239R, N240K, T242R; P40E, N61E, S87D, Q103E, S145D, S159K, S162K, K213L, P239R, N240K, T242R; S24R, N62R, P129E, S145D, P239R, K265N, Q275E; S24R, N61E, S87D, Q103E, P129E, A144K, Q206E, K213L, P239R, N240K, T242R; S24R, P40E, N61E, S87D, Q103E, P129E, A144K, S162K, Q206E, K213L, P239R, N240K, T242R; N61E, S87D, Q103E, P129E, S159K, S162K, K213L, N240K, T242R; S24R, P40E, N61E, Q103E, P129E, A144K, S145D, K213L, P239R, N240K, T242R; S24R, N61E, Q103E, P129E, S145D, P239R, N240K, T242R, K265N; S24R, N61E, Q103E, P129E, A144K, S145D, Q206E, K213L, P239R, N240K, T242R; S24R, P40E, N61E, Q103E, P129E, A144K, Q206E, K213L, P239R, N240K, T242R; N61E, Q103E, Q206E, K213L, P239R, N240K, T242R; P40E, N62R, S87D, Q103E, S162K; S24R, Q103E, P129E, S145D, Q206E, P239R, N240K, T242R, K265N; S24R, P40E, N61E, Q103E, P129E, A144K, K213L, P239R, N240K, T242R, K265N; N61E, N62R, S87D, Q103E, S159K, S162K, K213L, T242R, Q275E; P40E, N62R, S87D, Q103E, A144K, S159K, Q275E; N61E, Q103E, P129E, K213L, P239R, N240K, T242R; and S24R, N61E, Q103E, P129E, Q206E, K213L, P239R, N240K, T242R.

2. The fabric or dishware cleaning composition according to claim 1, wherein said cleaning composition is a laundry detergent.

3. The fabric or dishware cleaning composition of claim 2, wherein said fabric or dishware cleaning composition is a heavy duty liquid laundry detergent.

4. The fabric or dishware cleaning composition of claim 1, wherein said fabric or dishware cleaning composition is a dishware cleaning composition.

5. The fabric or dishware cleaning composition of claim 1, further comprising one or more additional enzymes or enzyme derivatives selected from the group consisting of hemicellulases, peroxidases, proteases, cellulases, xylanases, lipases, phospholipases, esterases, cutinases, pectinases, keratinases, reductases, oxidases, phenol oxidases, lipoxygenases, ligninases, pullulanases, tannases, pentosanases, mannanases, β-glucanases, arabinosidases, hyaluronidase, chondroitinase, laccase, amylases, and mixtures thereof.

6. The fabric or dishware cleaning composition of claim 1, further comprising at least one stabilizing agent.

7. The fabric or dishware cleaning composition of claim 1, comprising at least 0.0001 weight percent of the at least one subtilisin variant.

8. A method of cleaning, said method comprising the steps of: a) contacting a surface and/or an article comprising a fabric with the fabric or dishware cleaning composition of claim 1; and b) optionally washing and/or rinsing said surface or article.

* * * * *